United States Patent
Fukui et al.

(10) Patent No.: US 9,080,189 B2
(45) Date of Patent: *Jul. 14, 2015

(54) METHOD FOR PRODUCING AN ORGANIC ACID

(75) Inventors: Keita Fukui, Kawasaki (JP); Yoko Mihara, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 725 days.

This patent is subject to a terminal disclaimer.

(21) Appl. No.: 12/576,291

(22) Filed: Oct. 9, 2009

(65) Prior Publication Data

US 2010/0068774 A1    Mar. 18, 2010

Related U.S. Application Data

(63) Continuation of application No. PCT/JP2008/057086, filed on Apr. 10, 2008.

(30) Foreign Application Priority Data

Apr. 10, 2007 (JP) ................................. 2007-102668

(51) Int. Cl.
 *C12P 7/46* (2006.01)
(52) U.S. Cl.
 CPC ...................................... *C12P 7/46* (2013.01)
(58) Field of Classification Search
 None
 See application file for complete search history.

(56) References Cited

U.S. PATENT DOCUMENTS

| 5,142,834 | A | 9/1992 | Laclave et al. |
| 5,504,004 | A | 4/1996 | Guettler et al. |
| 2004/0030116 | A1 | 2/2004 | Pompejus et al. |
| 2006/0228712 | A1 | 10/2006 | Nakagawa et al. |
| 2007/0254345 | A1 | 11/2007 | Fukui et al. |
| 2008/0293113 | A1* | 11/2008 | Koseki et al. ................. 435/145 |

FOREIGN PATENT DOCUMENTS

| EP | 1672077 | 6/2006 |
| JP | 11-113588 | 4/1999 |
| JP | 1-196887 | 7/1999 |
| JP | 11-196888 | 7/1999 |
| JP | 2006-320208 | 11/2006 |
| WO | WO2007/046389 | 4/2007 |

OTHER PUBLICATIONS

GenBank Accession No. AJ303072 (Apr. 2005).*
G.E. de Vries et al. Cloning, Expression, and Sequence Analysis of the *Bacillus methanolicus* C1 Methanol Dehydrogenase Gene, J. Bacteriol. 174(16):5346-5353 (1992).*
J. Aarnikunnas et al. "The mannitol dehydrogenase gene (mdh) from *Leuconostoc mesenteroides* is distinct from other known bacterial mdh genes", Appl Microbiol Biotechnol 59:665-671. (2002).*
Guettler, M. V., et al, "*Actinobacilus succinogenes* sp. Nov., a novel succinic-acid-producing strain from the bovine rumen," Int. J. Systemic Bacteriol. 1999;49:207-216.
International Preliminary Report on Patentability for PCT Patent App. No. PCT/JP2008/057086 (Oct. 22, 2009).
Ikeda, M., et al., "The *Coynebacterium glutamicun* genome: features and impacts on biotechnological processes," Appl. Microbiol. Biotechnol. 2003;62:99-109.
Wang, Q., et al., "Expression of galactose permease and pyruvate carboxylase in *Escherichia coli ptsG* mutant increases the growth rate and succinate yield under anaerobic conditions," Biotechnol. Lett. 2006;28:89-93.
International Search Report for PCT Patent App. No. PCT/JP2008/057086 (Jul. 1, 2008).
Fukui, K., et al., "Identification of succinate exporter in *Corynebacterium glutamicum* and its physiological roles under anaerobic conditions," J. Biotechnol. 2011;154:25-34.
Huhn, S., et al., "Identification of the membrane protein SucE and its role in succinate transport in *Corynebacterium glutamicum*," Appl. Microbiol. Biotechnol. 2011;89:327-335.
Okino, S., et al., "Production of organic acids by *Corynebacterium glutamicum* under oxygen deprivation," Appl. Microbiol. Biotechnol. 2005;68:475-480.
Supplementary European Search Report for European Patent App. No. 08740187.3 (Jun. 23, 2014).

* cited by examiner

*Primary Examiner* — Rebecca Prouty
(74) *Attorney, Agent, or Firm* — Shelly Guest Cermak; Cermak Nakajima & McGowan LLP

(57) ABSTRACT

An organic acid is produced by allowing a bacterium which has an ability to produce an organic acid and has been modified so that expression of the sucE1 and mdh genes are enhanced, or a product obtained by processing the bacterium, to act on an organic raw material in a reaction mixture containing carbonate ions, bicarbonate ions, or carbon dioxide gas, and collecting the organic acid.

12 Claims, 1 Drawing Sheet

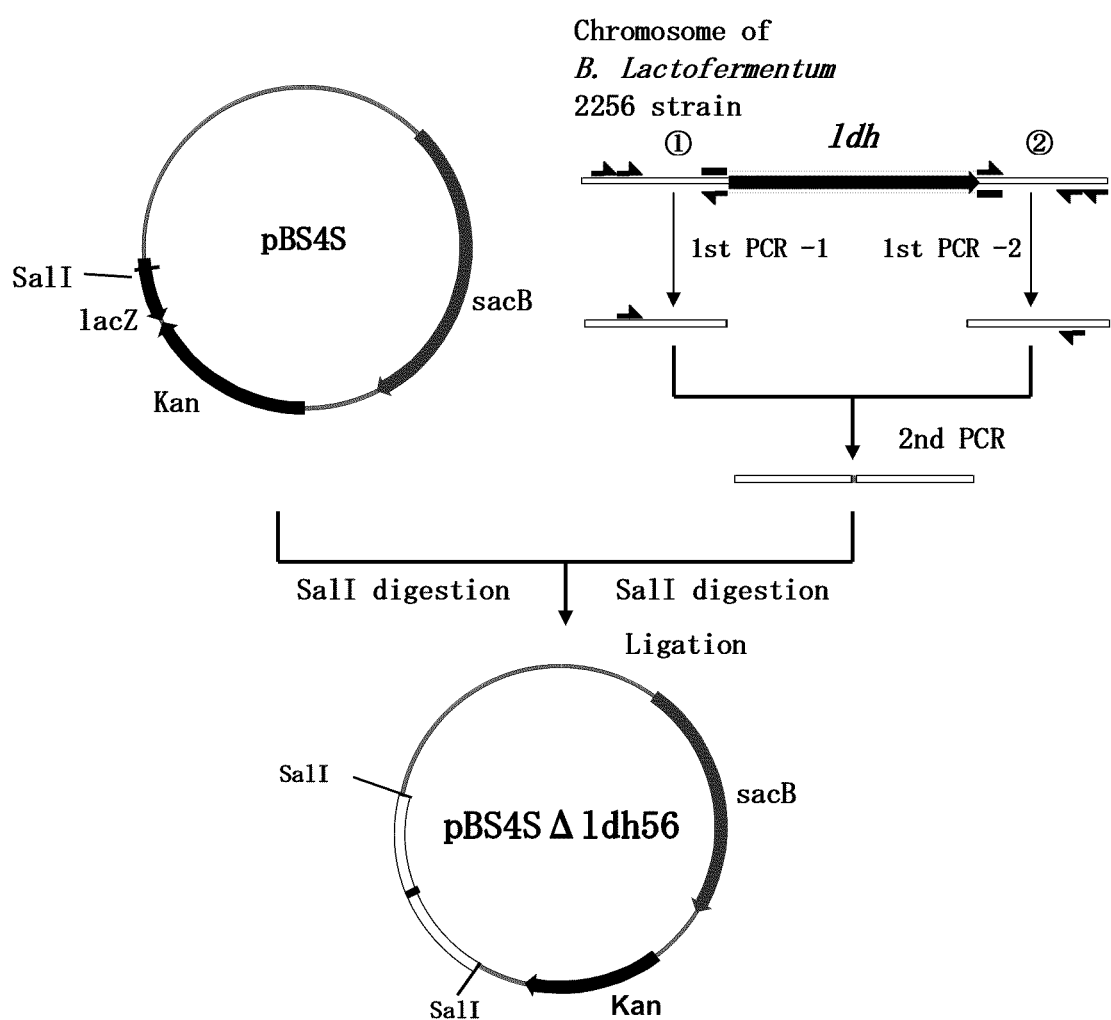

SEQUENCE LISTING

```
<160> NUMBER OF SEQ ID NOS: 45

<210> SEQ ID NO 1
<211> LENGTH: 33
<212> TYPE: DNA
<213> ORGANISM: Artificial
<220> FEATURE:
<223> OTHER INFORMATION: primer

<400> SEQUENCE: 1
gggcctgcag gaccaagacc gctgttgcag tga                                  33

<210> SEQ ID NO 2
<211> LENGTH: 31
<212> TYPE: DNA
<213> ORGANISM: Artificial
<220> FEATURE:
<223> OTHER INFORMATION: primer

<400> SEQUENCE: 2
gggcctgcag ggtattcaca ccagcccaa t                                     31

<210> SEQ ID NO 3
<211> LENGTH: 2330
<212> TYPE: DNA
<213> ORGANISM: Brevibacterium flavum
<220> FEATURE:
<221> NAME/KEY: CDS
<222> LOCATION: (571)..(2187)

<400> SEQUENCE: 3
gaccaagacc gctgttgcag tgaccactca gatggatgca gtgcaccgcg tcattggtct     60
gtgtggtgtt gtgctggtcg gcgagggctc ccctcaccgc ctgaagccaa tgcttgcgca    120
gcaaaagaag cgcctgaacc gcgtggcacc tggtgttccg gtgtatgaaa tcatcacggg    180
caacggcgaa ggccagaccc ctatcgcgaa gctgcagcgt gaactggtca agctgcctcg    240
```

```
caactacaag aagaacgacg tcgctgccct ggccgctcgc attgaggcta tggacaatgt      300
cggaaacgct cctggcggat ctttgcctaa gggtccattg ccaagggcg caagcatgtc       360 cggtatgaac cgccgtgctc gccgacaggc tgaacgcagg ggcgaggctt aaagcctttt      420
cgctttcgcg tcggcgccga agttttttaa aaagccgcac ttcaccaact tggatggggt      480 gcggttttg cgtgctctgg cttagggaac gtggccagtt ccacatcaaa taacgcagaa       540
gtagtactta atccatgaga tcatgaatgg gtg agc ttc ctt gta gaa aat caa       594
                                  Val Ser Phe Leu Val Glu Asn Gln
                                   1               5 tta ctc gcg ttg gtt gtc atc atg acg gtc gga cta ttg ctc ggc cgc        642
Leu Leu Ala Leu Val Val Ile Met Thr Val Gly Leu Leu Leu Gly Arg
 10              15                  20 atc aaa att ttc ggg ttc cgc ctc ggt gtg gcc gct gta ttg ttt gtc        690
Ile Lys Ile Phe Gly Phe Arg Leu Gly Val Ala Ala Val Leu Phe Val
 25              30                  35                  40 ggt ctg gcg ctg tcc acc att gag ccg gat att tcc gtc ccg ccg ctc        738
Gly Leu Ala Leu Ser Thr Ile Glu Pro Asp Ile Ser Val Pro Pro Leu
             45                  50                  55 att tat gtt gtt gga ctg tca ctt ttt gtc tac acc atc gga ctg gag        786
Ile Tyr Val Val Gly Leu Ser Leu Phe Val Tyr Thr Ile Gly Leu Glu
             60                  65                  70 gcc ggc ccc gga ttc ttc acc tcc atg aaa acc aca ggt ctg cgc aac        834
Ala Gly Pro Gly Phe Phe Thr Ser Met Lys Thr Thr Gly Leu Arg Asn
         75                  80                  85 aac gca ctg acc ttg ggc gcc atc atc gcc acc acg gca ctc gca tgg        882
Asn Ala Leu Thr Leu Gly Ala Ile Ile Ala Thr Thr Ala Leu Ala Trp
 90              95                 100 gca ctc atc acc gtt ttc aac atc gat gcc gcc tcc ggt gcc ggt atg        930
Ala Leu Ile Thr Val Phe Asn Ile Asp Ala Ala Ser Gly Ala Gly Met
105             110                 115                 120 ctc acc ggc gcg ctc acc aat acc cca gcc atg gcc gcg gtt gtt gac        978
Leu Thr Gly Ala Leu Thr Asn Thr Pro Ala Met Ala Ala Val Val Asp
             125                 130                 135 gca ctg cct tcg ctt atc gac gac acc ggc cag ctt cac atc atc gcc       1026
Ala Leu Pro Ser Leu Ile Asp Asp Thr Gly Gln Leu His Ile Ile Ala
             140                 145                 150 gag ttg ccc gtc gtc gca tat tcc ttg gca tac ccc ctc gga gtg ctc       1074
Glu Leu Pro Val Val Ala Tyr Ser Leu Ala Tyr Pro Leu Gly Val Leu
             155                 160                 165 atc gtt att ctc tcc atc gcg atc ttc agc tct gtg ttc aaa gtg gat       1122
Ile Val Ile Leu Ser Ile Ala Ile Phe Ser Ser Val Phe Lys Val Asp
             170                 175                 180 cac aat aaa gag gcc gaa gaa gca ggt gtc gcg gtc cag gaa ctc aaa       1170
His Asn Lys Glu Ala Glu Glu Ala Gly Val Ala Val Gln Glu Leu Lys
185                 190                 195                 200 ggc cgc cgc atc cgc gtc acc gtc gct gat ctt cca gcc ctg gag aat       1218
Gly Arg Arg Ile Arg Val Thr Val Ala Asp Leu Pro Ala Leu Glu Asn
             205                 210                 215 atc cca gag ctg ctc aat ctc cac gtc att gtg tcc cgc gtg gaa cga       1266
Ile Pro Glu Leu Leu Asn Leu His Val Ile Val Ser Arg Val Glu Arg
             220                 225                 230 gac ggt gag caa ttc ata ccg ctt tat ggc gaa cac gca cgc atc ggc       1314
Asp Gly Glu Gln Phe Ile Pro Leu Tyr Gly Glu His Ala Arg Ile Gly
             235                 240                 245 gat gtc tta aca gtg gtg ggt gcc gat gaa gaa ctc aac cgc gcg gaa       1362
Asp Val Leu Thr Val Val Gly Ala Asp Glu Glu Leu Asn Arg Ala Glu
250                 255                 260
```

```
aaa gcc atc ggt gaa ctc atc gac ggc gac ccc tac agc gat gtg gaa     1410
Lys Ala Ile Gly Glu Leu Ile Asp Gly Asp Pro Tyr Ser Asp Val Glu
265                 270                 275                 280 ctt gat tac cga cgc atc ttc gtc tca aac aca gaa gtc gtg ggc act     1458
Leu Asp Tyr Arg Arg Ile Phe Val Ser Asn Thr Glu Val Val Gly Thr
            285                 290                 295 ccc cta tcc aag ctc caa cca cta ttt aaa gac atg ctg atc acc cgt     1506
Pro Leu Ser Lys Leu Gln Pro Leu Phe Lys Asp Met Leu Ile Thr Arg
300                 305                 310 atc agg cgc ggc gac aca gat ttg gtg gcc tcc ccc gac atg act ttg     1554
Ile Arg Arg Gly Asp Thr Asp Leu Val Ala Ser Pro Asp Met Thr Leu
        315                 320                 325 cag cta ggt gat cgt gtc cgc gtt gtc gca cca aca gag aag ctc cgc     1602
Gln Leu Gly Asp Arg Val Arg Val Val Ala Pro Thr Glu Lys Leu Arg
    330                 335                 340 gaa gca acc cga cta ctg ggc gat tcc tac aaa aaa ctc tcc gat ttc     1650
Glu Ala Thr Arg Leu Leu Gly Asp Ser Tyr Lys Lys Leu Ser Asp Phe
345                 350                 355                 360 aac ctg ctc ccc ctc gct gcc ggc ctc atg atc ggt gtg ctt gtc ggc     1698
Asn Leu Leu Pro Leu Ala Ala Gly Leu Met Ile Gly Val Leu Val Gly
                365                 370                 375 atg gta gaa ttc cca cta cca ggt gga agc tcc ctg aaa ctg ggt aac     1746
Met Val Glu Phe Pro Leu Pro Gly Gly Ser Ser Leu Lys Leu Gly Asn
            380                 385                 390 gca ggt gga ccg cta gtt gtt gcg ctg ctc ggc atg att aat cgc         1794
Ala Gly Gly Pro Leu Val Val Ala Leu Leu Gly Met Ile Asn Arg
        395                 400                 405 aca ggc aag ttc gtc tgg caa atc ccc tac gga gca aac ctt gcc ctt     1842
Thr Gly Lys Phe Val Trp Gln Ile Pro Tyr Gly Ala Asn Leu Ala Leu
410                 415                 420 cgc caa ctg ggc atc aca cta ttt ttg gct gcc atc ggt acc tca gcg     1890
Arg Gln Leu Gly Ile Thr Leu Phe Leu Ala Ala Ile Gly Thr Ser Ala
425                 430                 435                 440 ggc gca gga ttt cga tca gcg atc agc gac ccc caa tca ctc acc atc     1938
Gly Ala Gly Phe Arg Ser Ala Ile Ser Asp Pro Gln Ser Leu Thr Ile
                445                 450                 455 atc ggc ttc ggt gcg ctg ctc act ttg ttc atc tcc atc acg gtc ctg     1986
Ile Gly Phe Gly Ala Leu Leu Thr Leu Phe Ile Ser Ile Thr Val Leu
            460                 465                 470 ttc gtt ggc cac aaa ctg atg aaa atc ccc ttc ggt gaa acc gct ggc     2034
Phe Val Gly His Lys Leu Met Lys Ile Pro Phe Gly Glu Thr Ala Gly
        475                 480                 485 atc ctc gcc ggt acg caa acc cac cct gct gtg ctg agt tat gtg tca     2082
Ile Leu Ala Gly Thr Gln Thr His Pro Ala Val Leu Ser Tyr Val Ser
490                 495                 500 gat gcc tcc cgc aac gag ctc cct gcc atg ggt tat acc tct gtg tat     2130
Asp Ala Ser Arg Asn Glu Leu Pro Ala Met Gly Tyr Thr Ser Val Tyr
505                 510                 515                 520 ccg ctg gcg atg atc gca aag atc ctg gcc gcc caa acg ttg ttg ttc     2178
Pro Leu Ala Met Ile Ala Lys Ile Leu Ala Ala Gln Thr Leu Leu Phe
                525                 530                 535 cta ctt atc tagcattgac cccttaagcg cagaaggcga tttaagggt              2227
Leu Leu Ile tgggttttcc cgatgactag ttggtccaga gcgtgtattt gaggccctta gggcgattc    2287 tggggctgat gttttgtgt ccattggggc tggtgtgaat acc                      2330

<210> SEQ ID NO 4
<211> LENGTH: 539
<212> TYPE: PRT
```

<213> ORGANISM: Brevibacterium flavum

<400> SEQUENCE: 4

```
Met Ser Phe Leu Val Glu Asn Gln Leu Leu Ala Leu Val Val Ile Met
1               5                   10                  15
Thr Val Gly Leu Leu Gly Arg Ile Lys Ile Phe Gly Phe Arg Leu
            20                  25                  30
Gly Val Ala Ala Val Leu Phe Val Gly Leu Ala Leu Ser Thr Ile Glu
            35                  40                  45
Pro Asp Ile Ser Val Pro Leu Ile Tyr Val Gly Leu Ser Leu
        50                  55                  60
Phe Val Tyr Thr Ile Gly Leu Glu Ala Gly Pro Gly Phe Phe Thr Ser
65                  70                  75                  80
Met Lys Thr Thr Gly Leu Arg Asn Asn Ala Leu Thr Leu Gly Ala Ile
                85                  90                  95
Ile Ala Thr Thr Ala Leu Ala Trp Ala Leu Ile Thr Val Phe Asn Ile
            100                 105                 110
Asp Ala Ala Ser Gly Ala Gly Met Leu Thr Gly Ala Leu Thr Asn Thr
            115                 120                 125
Pro Ala Met Ala Ala Val Val Asp Ala Leu Pro Ser Leu Ile Asp Asp
        130                 135                 140
Thr Gly Gln Leu His Ile Ile Ala Glu Leu Pro Val Val Ala Tyr Ser
145                 150                 155                 160
Leu Ala Tyr Pro Leu Gly Val Leu Ile Val Ile Leu Ser Ile Ala Ile
                165                 170                 175
Phe Ser Ser Val Phe Lys Val Asp His Asn Lys Glu Ala Glu Ala
            180                 185                 190
Gly Val Ala Val Gln Glu Leu Lys Gly Arg Arg Ile Arg Val Thr Val
            195                 200                 205
Ala Asp Leu Pro Ala Leu Glu Asn Ile Pro Glu Leu Leu Asn Leu His
        210                 215                 220
Val Ile Val Ser Arg Val Glu Arg Asp Gly Glu Gln Phe Ile Pro Leu
225                 230                 235                 240
Tyr Gly Glu His Ala Arg Ile Gly Asp Val Leu Thr Val Gly Ala
                245                 250                 255
Asp Glu Glu Leu Asn Arg Ala Glu Lys Ala Ile Gly Glu Leu Ile Asp
            260                 265                 270
Gly Asp Pro Tyr Ser Asp Val Glu Leu Asp Tyr Arg Arg Ile Phe Val
        275                 280                 285
Ser Asn Thr Glu Val Val Gly Thr Pro Leu Ser Lys Leu Gln Pro Leu
290                 295                 300
Phe Lys Asp Met Leu Ile Thr Arg Ile Arg Arg Gly Asp Thr Asp Leu
305                 310                 315                 320
Val Ala Ser Pro Asp Met Thr Leu Gln Leu Gly Asp Arg Val Arg Val
                325                 330                 335
Val Ala Pro Thr Glu Lys Leu Arg Glu Ala Thr Arg Leu Leu Gly Asp
            340                 345                 350
Ser Tyr Lys Lys Leu Ser Asp Phe Asn Leu Leu Pro Leu Ala Ala Gly
        355                 360                 365
Leu Met Ile Gly Val Leu Val Gly Met Val Glu Phe Pro Leu Pro Gly
        370                 375                 380
Gly Ser Ser Leu Lys Leu Gly Asn Ala Gly Gly Pro Leu Val Val Ala
385                 390                 395                 400
```

```
Leu Leu Leu Gly Met Ile Asn Arg Thr Gly Lys Phe Val Trp Gln Ile
                405                 410                 415
Pro Tyr Gly Ala Asn Leu Ala Leu Arg Gln Leu Gly Ile Thr Leu Phe
            420                 425                 430
Leu Ala Ala Ile Gly Thr Ser Ala Gly Ala Gly Phe Arg Ser Ala Ile
        435                 440                 445
Ser Asp Pro Gln Ser Leu Thr Ile Ile Gly Phe Gly Ala Leu Leu Thr
    450                 455                 460
Leu Phe Ile Ser Ile Thr Val Leu Phe Val Gly His Lys Leu Met Lys
465                 470                 475                 480
Ile Pro Phe Gly Glu Thr Ala Gly Ile Leu Ala Gly Thr Gln Thr His
                485                 490                 495
Pro Ala Val Leu Ser Tyr Val Ser Asp Ala Ser Arg Asn Glu Leu Pro
            500                 505                 510
Ala Met Gly Tyr Thr Ser Val Tyr Pro Leu Ala Met Ile Ala Lys Ile
        515                 520                 525
Leu Ala Ala Gln Thr Leu Leu Phe Leu Leu Ile
    530                 535
```

```
<210> SEQ ID NO 5
<211> LENGTH: 1620
<212> TYPE: DNA
<213> ORGANISM: Corynebacterium glutamicum
<220> FEATURE:
<221> NAME/KEY: CDS
<222> LOCATION: (1)..(1617)

<400> SEQUENCE: 5
```

```
gtg agc ttc ctt gta gaa aat caa tta ctc gcg ttg gtt gtc atc atg      48
Val Ser Phe Leu Val Glu Asn Gln Leu Leu Ala Leu Val Val Ile Met
1               5                   10                  15 acg gtc gga cta ttg ctc ggc cgc atc aaa att ttc ggg ttc cgt ctc      96
Thr Val Gly Leu Leu Leu Gly Arg Ile Lys Ile Phe Gly Phe Arg Leu
                20                  25                  30 ggc gtc gcc gct gta ctg ttt gta ggt cta gcg cta tcc acc att gag     144
Gly Val Ala Ala Val Leu Phe Val Gly Leu Ala Leu Ser Thr Ile Glu
            35                  40                  45 ccg gat att tcc gtc cca tcc ctc att tac gtg gtt gga ctg tcg ctt     192
Pro Asp Ile Ser Val Pro Ser Leu Ile Tyr Val Val Gly Leu Ser Leu
        50                  55                  60 ttt gtc tac acg atc ggt ctg gaa gcc ggc cct gga ttc ttc acc tcc     240
Phe Val Tyr Thr Ile Gly Leu Glu Ala Gly Pro Gly Phe Phe Thr Ser
65                  70                  75                  80 atg aaa acc act ggt ctg cgc aac aac gca ctg acc ttg ggc gcc atc     288
Met Lys Thr Thr Gly Leu Arg Asn Asn Ala Leu Thr Leu Gly Ala Ile
                85                  90                  95 atc gcc acc acg gca ctc gca tgg gca ctc atc aca gtt ttg aac atc     336
Ile Ala Thr Thr Ala Leu Ala Trp Ala Leu Ile Thr Val Leu Asn Ile
            100                 105                 110 gat gcc gcc tcc ggc gcc ggc atg ctc acc ggc gcg ctc acc aac acc     384
Asp Ala Ala Ser Gly Ala Gly Met Leu Thr Gly Ala Leu Thr Asn Thr
        115                 120                 125 cca gcc atg gcc gca gtt gtt gac gca ctt cct tcg ctt atc gac gac     432
Pro Ala Met Ala Ala Val Val Asp Ala Leu Pro Ser Leu Ile Asp Asp
    130                 135                 140 acc ggc cag ctt cac ctc atc gcc gag ctg ccc gtc gtc gca tat tcc     480
Thr Gly Gln Leu His Leu Ile Ala Glu Leu Pro Val Val Ala Tyr Ser
145                 150                 155                 160 ttg gca tac ccc ctc ggt gtg ctc atc gtt att ctc tcc atc gcc atc     528
Leu Ala Tyr Pro Leu Gly Val Leu Ile Val Ile Leu Ser Ile Ala Ile
```

|     |     |     |     |     |     |     |     |     |     |     |     |      |
|-----|-----|-----|-----|-----|-----|-----|-----|-----|-----|-----|-----|------|
| Leu | Ala | Tyr | Pro | Leu | Gly | Val | Leu | Ile | Val | Ile | Leu | Ser | Ile | Ala | Ile |
|     |     |     | 165 |     |     |     | 170 |     |     |     | 175 |      |

```
ttc agc tct gtg ttc aaa gtc gac cac aac aaa gaa gcc gaa gaa gcg      576
Phe Ser Ser Val Phe Lys Val Asp His Asn Lys Glu Ala Glu Glu Ala
        180                     185                     190 ggc gtt gcg gtc cag gaa ctc aaa ggc cgt cgc atc cgc gtc acc gtc      624
Gly Val Ala Val Gln Glu Leu Lys Gly Arg Arg Ile Arg Val Thr Val
        195                     200                     205 gct gat ctt cca gcc ctg gag aac atc cca gag ctg ctc aac ctc cac      672
Ala Asp Leu Pro Ala Leu Glu Asn Ile Pro Glu Leu Leu Asn Leu His
    210                     215                     220 gtc att gtg tcc cga gtg gaa cga gac ggt gag caa ttc atc ccg ctt      720
Val Ile Val Ser Arg Val Glu Arg Asp Gly Glu Gln Phe Ile Pro Leu
225                     230                     235                 240 tat ggc gaa cac gca cgc atc ggc gat gtc tta aca gtg gtg ggt gcc      768
Tyr Gly Glu His Ala Arg Ile Gly Asp Val Leu Thr Val Val Gly Ala
                245                     250                     255 gat gaa gaa ctc aac cgc gcg gaa aaa gcc atc ggt gaa ctc att gac      816
Asp Glu Glu Leu Asn Arg Ala Glu Lys Ala Ile Gly Glu Leu Ile Asp
        260                     265                     270 ggc gac ccc tac agc aat gtg gaa ctt gat tac cga cgc atc ttc gtc      864
Gly Asp Pro Tyr Ser Asn Val Glu Leu Asp Tyr Arg Arg Ile Phe Val
        275                     280                     285 tca aac aca gca gtc gtg ggc act ccc cta tcc aag ctc cag cca ctg      912
Ser Asn Thr Ala Val Val Gly Thr Pro Leu Ser Lys Leu Gln Pro Leu
    290                     295                     300 ttt aaa gac atg ctg atc acc cgc atc agg cgc ggc gac aca gat ttg      960
Phe Lys Asp Met Leu Ile Thr Arg Ile Arg Arg Gly Asp Thr Asp Leu
305                     310                     315                 320 gtg gcc tcc tcc gac atg act ttg cag ctc ggt gac cgt gtc cgc gtt     1008
Val Ala Ser Ser Asp Met Thr Leu Gln Leu Gly Asp Arg Val Arg Val
                325                     330                     335 gtc gca cca gca gaa aaa ctc cgc gaa gca acc caa ttg ctc ggc gat     1056
Val Ala Pro Ala Glu Lys Leu Arg Glu Ala Thr Gln Leu Leu Gly Asp
        340                     345                     350 tcc tac aag aaa ctc tcc gat ttc aac ctg ctc cca ctc gct gcc ggc     1104
Ser Tyr Lys Lys Leu Ser Asp Phe Asn Leu Leu Pro Leu Ala Ala Gly
        355                     360                     365 ctc atg atc ggt gtg ctt gtc ggc atg gtg gag ttc cca cta cca ggt     1152
Leu Met Ile Gly Val Leu Val Gly Met Val Glu Phe Pro Leu Pro Gly
    370                     375                     380 gga agc tcc ctg aaa ctg ggt aac gca ggt gga ccg cta gtt gtt gcg     1200
Gly Ser Ser Leu Lys Leu Gly Asn Ala Gly Gly Pro Leu Val Val Ala
385                     390                     395                 400 ctg ctc ctc ggc atg atc aat cgc aca ggc aag ttc gtc tgg caa atc     1248
Leu Leu Leu Gly Met Ile Asn Arg Thr Gly Lys Phe Val Trp Gln Ile
                405                     410                     415 ccc tac gga gca aac ctt gcc ctt cgc caa ctg ggc atc aca cta ttt     1296
Pro Tyr Gly Ala Asn Leu Ala Leu Arg Gln Leu Gly Ile Thr Leu Phe
        420                     425                     430 ttg gct gcc atc ggt acc tca gcg ggc gca gga ttt cga tca gcg atc     1344
Leu Ala Ala Ile Gly Thr Ser Ala Gly Ala Gly Phe Arg Ser Ala Ile
        435                     440                     445 agc gac ccc caa tca ctc acc atc atc ggc ttc ggt gcg ctg ctc act     1392
Ser Asp Pro Gln Ser Leu Thr Ile Ile Gly Phe Gly Ala Leu Leu Thr
    450                     455                     460 ttg ttc atc tcc atc acg gtg ctg ttc gtt ggc cac aaa ctg atg aaa     1440
Leu Phe Ile Ser Ile Thr Val Leu Phe Val Gly His Lys Leu Met Lys
465                     470                     475                 480
```

```
atc ccc ttc ggt gaa acc gct ggc atc ctc gcc ggt acg caa acc cac        1488
Ile Pro Phe Gly Glu Thr Ala Gly Ile Leu Ala Gly Thr Gln Thr His
                485                 490                 495 cct gct gtg ctg agt tat gtg tca gat gcc tcc cgc aac gag ctc cct        1536
Pro Ala Val Leu Ser Tyr Val Ser Asp Ala Ser Arg Asn Glu Leu Pro
            500                 505                 510 gcc atg ggt tat acc tct gtg tat ccg ctg gcg atg atc gca aag atc        1584
Ala Met Gly Tyr Thr Ser Val Tyr Pro Leu Ala Met Ile Ala Lys Ile
        515                 520                 525 ctg gcc gcc caa acg ttg ttg ttc cta ctt atc tag                        1620
Leu Ala Ala Gln Thr Leu Leu Phe Leu Leu Ile
    530                 535
```

<210> SEQ ID NO 6
<211> LENGTH: 539
<212> TYPE: PRT
<213> ORGANISM: Corynebacterium glutamicum

<400> SEQUENCE: 6

```
Met Ser Phe Leu Val Glu Asn Gln Leu Leu Ala Leu Val Val Ile Met
1               5                   10                  15

Thr Val Gly Leu Leu Gly Arg Ile Lys Ile Phe Gly Phe Arg Leu
            20                  25                  30

Gly Val Ala Ala Val Leu Phe Val Gly Leu Ala Leu Ser Thr Ile Glu
        35                  40                  45

Pro Asp Ile Ser Val Pro Ser Leu Ile Tyr Val Val Gly Leu Ser Leu
    50                  55                  60

Phe Val Tyr Thr Ile Gly Leu Glu Ala Gly Pro Gly Phe Phe Thr Ser
65                  70                  75                  80

Met Lys Thr Thr Gly Leu Arg Asn Asn Ala Leu Thr Leu Gly Ala Ile
                85                  90                  95

Ile Ala Thr Thr Ala Leu Ala Trp Ala Leu Ile Thr Val Leu Asn Ile
            100                 105                 110

Asp Ala Ala Ser Gly Ala Gly Met Leu Thr Gly Ala Leu Thr Asn Thr
        115                 120                 125

Pro Ala Met Ala Ala Val Asp Ala Leu Pro Ser Leu Ile Asp Asp
    130                 135                 140

Thr Gly Gln Leu His Leu Ile Ala Glu Leu Pro Val Val Ala Tyr Ser
145                 150                 155                 160

Leu Ala Tyr Pro Leu Gly Val Leu Ile Val Ile Leu Ser Ile Ala Ile
                165                 170                 175

Phe Ser Ser Val Phe Lys Val Asp His Asn Lys Glu Ala Glu Ala
            180                 185                 190

Gly Val Ala Val Gln Glu Leu Lys Gly Arg Arg Ile Arg Val Thr Val
        195                 200                 205

Ala Asp Leu Pro Ala Leu Glu Asn Ile Pro Glu Leu Leu Asn Leu His
    210                 215                 220

Val Ile Val Ser Arg Val Glu Arg Asp Gly Glu Gln Phe Ile Pro Leu
225                 230                 235                 240

Tyr Gly Glu His Ala Arg Ile Gly Asp Val Leu Thr Val Val Gly Ala
                245                 250                 255

Asp Glu Glu Leu Asn Arg Ala Glu Lys Ala Ile Gly Glu Leu Ile Asp
            260                 265                 270

Gly Asp Pro Tyr Ser Asn Val Glu Leu Asp Tyr Arg Arg Ile Phe Val
        275                 280                 285

Ser Asn Thr Ala Val Val Gly Thr Pro Leu Ser Lys Leu Gln Pro Leu
```

```
                290                    295                       300
Phe Lys Asp Met Leu Ile Thr Arg Ile Arg Arg Gly Asp Thr Asp Leu
305                 310                   315                   320

Val Ala Ser Ser Asp Met Thr Leu Gln Leu Gly Asp Arg Val Arg Val
                325                   330                   335

Val Ala Pro Ala Glu Lys Leu Arg Glu Ala Thr Gln Leu Leu Gly Asp
                340                   345                   350

Ser Tyr Lys Lys Leu Ser Asp Phe Asn Leu Leu Pro Leu Ala Ala Gly
            355                   360                   365

Leu Met Ile Gly Val Leu Val Gly Met Val Glu Phe Pro Leu Pro Gly
        370                   375                   380

Gly Ser Ser Leu Lys Leu Gly Asn Ala Gly Gly Pro Leu Val Val Ala
385                 390                   395                   400

Leu Leu Leu Gly Met Ile Asn Arg Thr Gly Lys Phe Val Trp Gln Ile
                405                   410                   415

Pro Tyr Gly Ala Asn Leu Ala Leu Arg Gln Leu Gly Ile Thr Leu Phe
                420                   425                   430

Leu Ala Ala Ile Gly Thr Ser Ala Gly Ala Gly Phe Arg Ser Ala Ile
                435                   440                   445

Ser Asp Pro Gln Ser Leu Thr Ile Ile Gly Phe Gly Ala Leu Leu Thr
450                 455                   460

Leu Phe Ile Ser Ile Thr Val Leu Phe Val Gly His Lys Leu Met Lys
465                 470                   475                   480

Ile Pro Phe Gly Glu Thr Ala Gly Ile Leu Ala Gly Thr Gln Thr His
                485                   490                   495

Pro Ala Val Leu Ser Tyr Val Ser Asp Ala Ser Arg Asn Glu Leu Pro
                500                   505                   510

Ala Met Gly Tyr Thr Ser Val Tyr Pro Leu Ala Met Ile Ala Lys Ile
            515                   520                   525

Leu Ala Ala Gln Thr Leu Leu Phe Leu Leu Ile
        530                   535

<210> SEQ ID NO 7
<211> LENGTH: 1629
<212> TYPE: DNA
<213> ORGANISM: Corynebacterium efficiens
<220> FEATURE:
<221> NAME/KEY: CDS
<222> LOCATION: (1)..(1626)

<400> SEQUENCE: 7 gtg agc att ttc gtg gaa aat cag ttg ttg gcc ctg gtg gcc atc atg      48
Val Ser Ile Phe Val Glu Asn Gln Leu Leu Ala Leu Val Ala Ile Met
1               5                   10                  15 ggt atc ggt ctg ttg ctc ggc cgg atc agg ttc ttc ggg ttc cgg ctc      96
Gly Ile Gly Leu Leu Leu Gly Arg Ile Arg Phe Phe Gly Phe Arg Leu
            20                  25                  30 ggg gtg gcg gcg gtg ttg ttc gtg ggt ctg gcc ttc tcc acc atc gaa     144
Gly Val Ala Ala Val Leu Phe Val Gly Leu Ala Phe Ser Thr Ile Glu
        35                  40                  45 ccg gac atc acg gtg cct ccc ctg atc tac gtg gtg ggc ctg gcc ctg     192
Pro Asp Ile Thr Val Pro Pro Leu Ile Tyr Val Val Gly Leu Ala Leu
    50                  55                  60 ttt gtg tac acc atc ggg ctg gag gcc ggc cgt gac ttc ttc agg tcg     240
Phe Val Tyr Thr Ile Gly Leu Glu Ala Gly Arg Asp Phe Phe Arg Ser
65                  70                  75                  80 ctg cgg tcc acc ggc ctg cgt aac aac ggg ctg gcc ctc ggt gcc atc     288
```

```
        Leu Arg Ser Thr Gly Leu Arg Asn Asn Gly Leu Ala Leu Gly Ala Ile
                        85                  90                  95 atc gcc acc acc gcg atc gcc tgg gtg gtc atc aag gcg ctg ggc ctg      336
Ile Ala Thr Thr Ala Ile Ala Trp Val Val Ile Lys Ala Leu Gly Leu
            100                 105                 110 gca ccc gcg acg ggt gcc ggc atg ttg acc ggt gcg ctg acc aac acc      384
Ala Pro Ala Thr Gly Ala Gly Met Leu Thr Gly Ala Leu Thr Asn Thr
                115                 120                 125 ccg gcg atg gcg gcg gtg gtc gac gcc cta ccg gcg ctt atc gac gac      432
Pro Ala Met Ala Ala Val Val Asp Ala Leu Pro Ala Leu Ile Asp Asp
        130                 135                 140 aac ccc acc gac gca gca cgc atc ctg gag ctg cct gtg gtg gcc tat      480
Asn Pro Thr Asp Ala Ala Arg Ile Leu Glu Leu Pro Val Val Ala Tyr
145                 150                 155                 160 tcc ctc acc tac ccg ctc ggt gtc ctg gtg gtg atc ctc acg atc gcg      528
Ser Leu Thr Tyr Pro Leu Gly Val Leu Val Val Ile Leu Thr Ile Ala
                    165                 170                 175 gtc tgc ggg ggc ctg ttc aag gtc aac cat gag aag gag gcg aag aat      576
Val Cys Gly Gly Leu Phe Lys Val Asn His Glu Lys Glu Ala Lys Asn
                180                 185                 190 gcc ggc gtg gcc gtt cag gag ctg acg gga cgc cgt gtc cgg gtc acc      624
Ala Gly Val Ala Val Gln Glu Leu Thr Gly Arg Arg Val Arg Val Thr
        195                 200                 205 cgg gat gat ctg ccc gcc atc agc aat atc ccg gaa ctg ctg gac ctg      672
Arg Asp Asp Leu Pro Ala Ile Ser Asn Ile Pro Glu Leu Leu Asp Leu
    210                 215                 220 gag gtc atc gtc tcc cgt gtg gag cgc cgg ggg cag cat gac cag ttc      720
Glu Val Ile Val Ser Arg Val Glu Arg Arg Gly Gln His Asp Gln Phe
225                 230                 235                 240 atc ccc gag gag ggt gat cgc acc cgg ttg ggt gac att ctc acc gtg      768
Ile Pro Glu Glu Gly Asp Arg Thr Arg Leu Gly Asp Ile Leu Thr Val
                    245                 250                 255 gtg ggc tcc gat gat gag ctc gag cgc gcg gtg ggt ctg ctc ggc gaa      816
Val Gly Ser Asp Asp Glu Leu Glu Arg Ala Val Gly Leu Leu Gly Glu
                260                 265                 270 ttc gtc gac ggc cat cca tac agc gat atc gat ctg gat tac cgc agg      864
Phe Val Asp Gly His Pro Tyr Ser Asp Ile Asp Leu Asp Tyr Arg Arg
        275                 280                 285 atc ttc gtc tct gat gaa tcc atg gtc ggt gtg ccc ttg gcg aaa ctg      912
Ile Phe Val Ser Asp Glu Ser Met Val Gly Val Pro Leu Ala Lys Leu
    290                 295                 300 cgc aac cgt att ccc ggc atg ttg atc acc cgg atc agg cgg ggt gac      960
Arg Asn Arg Ile Pro Gly Met Leu Ile Thr Arg Ile Arg Arg Gly Asp
305                 310                 315                 320 acc gac ctg att gcg cat ccg gat atg acc ctc cag ctg ggt gat ctg     1008
Thr Asp Leu Ile Ala His Pro Asp Met Thr Leu Gln Leu Gly Asp Leu
                    325                 330                 335 gtc cgc gtg gtt gcc ccc gcc gag cgg atc aag gag gcc acc cac atc     1056
Val Arg Val Val Ala Pro Ala Glu Arg Ile Lys Glu Ala Thr His Ile
                340                 345                 350 ttc ggt gac tcc tac aaa cgc ctc gct gat ttc aat ctg gtt ccc ctg     1104
Phe Gly Asp Ser Tyr Lys Arg Leu Ala Asp Phe Asn Leu Val Pro Leu
        355                 360                 365 gtg gtc ggt ctc tcc ctc ggg gtg ctg gtg ggc atg atg gaa ttc ccc     1152
Val Val Gly Leu Ser Leu Gly Val Leu Val Gly Met Met Glu Phe Pro
    370                 375                 380 ctg ccc ggt gga agc gcc ctg tcc ctg ggc aat gcc ggt ggg ccc ctg     1200
Leu Pro Gly Gly Ser Ala Leu Ser Leu Gly Asn Ala Gly Gly Pro Leu
385                 390                 395                 400
```

```
ttg atc gcg ctg ctg ctg ggg gcg atg ggc cgc acc ggc aag gtc gtc      1248
Leu Ile Ala Leu Leu Leu Gly Ala Met Gly Arg Thr Gly Lys Val Val
            405                 410                 415 tgg cag atc ccc tac agt gcc aac ctc gcc ctc cga cag ctg ggc atc      1296
Trp Gln Ile Pro Tyr Ser Ala Asn Leu Ala Leu Arg Gln Leu Gly Ile
            420                 425                 430 acc atg ttt ctg gcg gcc atc ggg acg acc gcg ggt gcc ggg ttc cgg      1344
Thr Met Phe Leu Ala Ala Ile Gly Thr Thr Ala Gly Ala Gly Phe Arg
            435                 440                 445 tcc gcg ctg agc gat ccg gcc tcc ctg ctg atc atc ggg gtg ggt gcc      1392
Ser Ala Leu Ser Asp Pro Ala Ser Leu Leu Ile Ile Gly Val Gly Ala
            450                 455                 460 ctg ctg acc ctg gtg atc tcc gtg ctg gtt ctt gtc atc ggg cac aag      1440
Leu Leu Thr Leu Val Ile Ser Val Leu Val Leu Val Ile Gly His Lys
465                 470                 475                 480 gtc atg cgt atc ccc ttc ggc gag acc gcc ggc atc ctc gcc ggc acc      1488
Val Met Arg Ile Pro Phe Gly Glu Thr Ala Gly Ile Leu Ala Gly Thr
                485                 490                 495 cag acc cat cct gcg gtg ttg agc tac ata tcg gag gcc tcg cgc aat      1536
Gln Thr His Pro Ala Val Leu Ser Tyr Ile Ser Glu Ala Ser Arg Asn
            500                 505                 510 gaa ctg ccg gcg atg ggt tac acc tcc gtc tat ccc ctc gcc atg gtg      1584
Glu Leu Pro Ala Met Gly Tyr Thr Ser Val Tyr Pro Leu Ala Met Val
            515                 520                 525 gcg aag atc atc gcc gca cag gtg ctg ttg ttc ctg ctg ata tag          1629
Ala Lys Ile Ile Ala Ala Gln Val Leu Leu Phe Leu Leu Ile
            530                 535                 540

<210> SEQ ID NO 8
<211> LENGTH: 542
<212> TYPE: PRT
<213> ORGANISM: Corynebacterium efficiens

<400> SEQUENCE: 8

Met Ser Ile Phe Val Glu Asn Gln Leu Leu Ala Leu Val Ala Ile Met
1               5                   10                  15

Gly Ile Gly Leu Leu Gly Arg Ile Arg Phe Phe Gly Phe Arg Leu
            20                  25                  30

Gly Val Ala Ala Val Leu Phe Val Gly Leu Ala Phe Ser Thr Ile Glu
        35                  40                  45

Pro Asp Ile Thr Val Pro Pro Leu Ile Tyr Val Gly Leu Ala Leu
    50                  55                  60

Phe Val Tyr Thr Ile Gly Leu Glu Ala Gly Arg Asp Phe Phe Arg Ser
65                  70                  75                  80

Leu Arg Ser Thr Gly Leu Arg Asn Asn Gly Leu Ala Leu Gly Ala Ile
                85                  90                  95

Ile Ala Thr Thr Ala Ile Ala Trp Val Val Lys Ala Leu Gly Leu
            100                 105                 110

Ala Pro Ala Thr Gly Ala Gly Met Leu Thr Gly Ala Leu Thr Asn Thr
        115                 120                 125

Pro Ala Met Ala Ala Val Val Asp Ala Leu Pro Ala Leu Ile Asp Asp
    130                 135                 140

Asn Pro Thr Asp Ala Ala Arg Ile Leu Glu Leu Pro Val Ala Tyr
145                 150                 155                 160

Ser Leu Thr Tyr Pro Leu Gly Val Leu Val Ile Leu Thr Ile Ala
                165                 170                 175

Val Cys Gly Gly Leu Phe Lys Val Asn His Glu Lys Glu Ala Lys Asn
            180                 185                 190
```

```
Ala Gly Val Ala Val Gln Glu Leu Thr Gly Arg Arg Val Arg Val Thr
        195                 200                 205
Arg Asp Asp Leu Pro Ala Ile Ser Asn Ile Pro Glu Leu Leu Asp Leu
210                 215                 220
Glu Val Ile Val Ser Arg Val Glu Arg Gly Gln His Asp Gln Phe
225                 230                 235                 240
Ile Pro Glu Glu Gly Asp Arg Thr Arg Leu Gly Asp Ile Leu Thr Val
                245                 250                 255
Val Gly Ser Asp Asp Glu Leu Glu Arg Ala Val Gly Leu Leu Gly Glu
                260                 265                 270
Phe Val Asp Gly His Pro Tyr Ser Asp Ile Asp Leu Asp Tyr Arg Arg
            275                 280                 285
Ile Phe Val Ser Asp Glu Ser Met Val Gly Val Pro Leu Ala Lys Leu
        290                 295                 300
Arg Asn Arg Ile Pro Gly Met Leu Ile Thr Arg Ile Arg Arg Gly Asp
305                 310                 315                 320
Thr Asp Leu Ile Ala His Pro Asp Met Thr Leu Gln Leu Gly Asp Leu
                325                 330                 335
Val Arg Val Ala Pro Ala Glu Arg Ile Lys Glu Ala Thr His Ile
                340                 345                 350
Phe Gly Asp Ser Tyr Lys Arg Leu Ala Asp Phe Asn Leu Val Pro Leu
            355                 360                 365
Val Val Gly Leu Ser Leu Gly Val Leu Val Gly Met Met Glu Phe Pro
        370                 375                 380
Leu Pro Gly Gly Ser Ala Leu Ser Leu Gly Asn Ala Gly Gly Pro Leu
385                 390                 395                 400
Leu Ile Ala Leu Leu Gly Ala Met Gly Arg Thr Gly Lys Val Val
                405                 410                 415
Trp Gln Ile Pro Tyr Ser Ala Asn Leu Ala Leu Arg Gln Leu Gly Ile
                420                 425                 430
Thr Met Phe Leu Ala Ala Ile Gly Thr Thr Ala Gly Ala Gly Phe Arg
            435                 440                 445
Ser Ala Leu Ser Asp Pro Ala Ser Leu Leu Ile Gly Val Gly Ala
        450                 455                 460
Leu Leu Thr Leu Val Ile Ser Val Leu Val Leu Val Ile Gly His Lys
465                 470                 475                 480
Val Met Arg Ile Pro Phe Gly Glu Thr Ala Gly Ile Leu Ala Gly Thr
                485                 490                 495
Gln Thr His Pro Ala Val Leu Ser Tyr Ile Ser Glu Ala Ser Arg Asn
            500                 505                 510
Glu Leu Pro Ala Met Gly Tyr Thr Ser Val Tyr Pro Leu Ala Met Val
        515                 520                 525
Ala Lys Ile Ile Ala Ala Gln Val Leu Leu Phe Leu Leu Ile
530                 535                 540

<210> SEQ ID NO 9
<211> LENGTH: 3423
<212> TYPE: DNA
<213> ORGANISM: Corynebacterium glutamicum
<220> FEATURE:
<221> NAME/KEY: CDS
<222> LOCATION: (1)..(3420)

<400> SEQUENCE: 9 atg tcg act cac aca tct tca acg ctt cca gca ttc aaa aag atc ttg        48
```

```
            Met Ser Thr His Thr Ser Ser Thr Leu Pro Ala Phe Lys Lys Ile Leu
            1               5                   10                  15 gta gca aac cgc ggc gaa atc gcg gtc cgt gct ttc cgt gca gca ctc         96
Val Ala Asn Arg Gly Glu Ile Ala Val Arg Ala Phe Arg Ala Ala Leu
                20                  25                  30 gaa acc ggt gca gcc acg gta gct att tac ccc cgt gaa gat cgg gga        144
Glu Thr Gly Ala Ala Thr Val Ala Ile Tyr Pro Arg Glu Asp Arg Gly
            35                  40                  45 tca ttc cac cgc tct ttt gct tct gaa gct gtc cgc att ggt act gaa        192
Ser Phe His Arg Ser Phe Ala Ser Glu Ala Val Arg Ile Gly Thr Glu
        50                  55                  60 ggc tca cca gtc aag gcg tac ctg gac atc gat gaa att atc ggt gca        240
Gly Ser Pro Val Lys Ala Tyr Leu Asp Ile Asp Glu Ile Ile Gly Ala
65              70                  75                  80 gct aaa aaa gtt aaa gca gat gct att tac ccg gga tat ggc ttc ctg        288
Ala Lys Lys Val Lys Ala Asp Ala Ile Tyr Pro Gly Tyr Gly Phe Leu
                85                  90                  95 tct gaa aat gcc cag ctt gcc cgc gag tgc gcg gaa aac ggc att act        336
Ser Glu Asn Ala Gln Leu Ala Arg Glu Cys Ala Glu Asn Gly Ile Thr
            100                 105                 110 ttt att ggc cca acc cca gag gtt ctt gat ctc acc ggt gat aag tct        384
Phe Ile Gly Pro Thr Pro Glu Val Leu Asp Leu Thr Gly Asp Lys Ser
        115                 120                 125 cgt gcg gta acc gcc gcg aag aag gct ggt ctg cca gtt ttg gcg gaa        432
Arg Ala Val Thr Ala Ala Lys Lys Ala Gly Leu Pro Val Leu Ala Glu
130                 135                 140 tcc acc ccg agc aaa aac atc gat gac atc gtt aaa agc gct gaa ggc        480
Ser Thr Pro Ser Lys Asn Ile Asp Asp Ile Val Lys Ser Ala Glu Gly
145                 150                 155                 160 cag act tac ccc atc ttt gta aag gca gtt gcc ggt ggt ggc gga cgc        528
Gln Thr Tyr Pro Ile Phe Val Lys Ala Val Ala Gly Gly Gly Gly Arg
                165                 170                 175 ggt atg cgc ttt gtt tct tca cct gat gag ctt cgc aaa ttg gca aca        576
Gly Met Arg Phe Val Ser Ser Pro Asp Glu Leu Arg Lys Leu Ala Thr
            180                 185                 190 gaa gca tct cgt gaa gct gaa gcg gca ttc ggc gac ggt tcg gta tat        624
Glu Ala Ser Arg Glu Ala Glu Ala Ala Phe Gly Asp Gly Ser Val Tyr
        195                 200                 205 gtc gag cgt gct gtg att aac ccc cag cac att gaa gtg cag atc ctt        672
Val Glu Arg Ala Val Ile Asn Pro Gln His Ile Glu Val Gln Ile Leu
210                 215                 220 ggc gat cgc act gga gaa gtt gta cac ctt tat gaa cgt gac tgc tca        720
Gly Asp Arg Thr Gly Glu Val Val His Leu Tyr Glu Arg Asp Cys Ser
225                 230                 235                 240 ctg cag cgt cgt cac caa aaa gtt gtc gaa att gcg cca gca cag cat        768
Leu Gln Arg Arg His Gln Lys Val Val Glu Ile Ala Pro Ala Gln His
                245                 250                 255 ttg gat cca gaa ctg cgt gat cgc att tgt gcg gat gca gta aag ttc        816
Leu Asp Pro Glu Leu Arg Asp Arg Ile Cys Ala Asp Ala Val Lys Phe
            260                 265                 270 tgc cgc tcc att ggt tac cag ggc gcg gga act gtg gaa ttc ttg gtc        864
Cys Arg Ser Ile Gly Tyr Gln Gly Ala Gly Thr Val Glu Phe Leu Val
        275                 280                 285 gat gaa aag ggc aac cac gtt ttc atc gaa atg aac cca cgt atc cag        912
Asp Glu Lys Gly Asn His Val Phe Ile Glu Met Asn Pro Arg Ile Gln
            290                 295                 300 gtt gag cac acc gtg act gaa gaa gtc acc gag gtg gac ctg gtg aag        960
Val Glu His Thr Val Thr Glu Glu Val Thr Glu Val Asp Leu Val Lys
305                 310                 315                 320
```

```
gcg cag atg cgc ttg gct gct ggt gca acc ttg aag gaa ttg ggt ctg    1008
Ala Gln Met Arg Leu Ala Ala Gly Ala Thr Leu Lys Glu Leu Gly Leu
            325                 330                 335 acc caa gat aag atc aag acc cac ggt gcg gca ctg cag tgc cgc atc    1056
Thr Gln Asp Lys Ile Lys Thr His Gly Ala Ala Leu Gln Cys Arg Ile
            340                 345                 350 acc acg gaa gat cca aac aac ggc ttc cgc cca gat acc gga act atc    1104
Thr Thr Glu Asp Pro Asn Asn Gly Phe Arg Pro Asp Thr Gly Thr Ile
        355                 360                 365 acc gcg tac cgc tca cca ggc gga gct ggc gtt cgt ctt gac ggt gca    1152
Thr Ala Tyr Arg Ser Pro Gly Gly Ala Gly Val Arg Leu Asp Gly Ala
        370                 375                 380 gct cag ctc ggt ggc gaa atc acc gca cac ttt gac tcc atg ctg gtg    1200
Ala Gln Leu Gly Gly Glu Ile Thr Ala His Phe Asp Ser Met Leu Val
385                 390                 395                 400 aaa atg acc tgc cgt ggt tcc gat ttt gaa act gct gtt gct cgt gca    1248
Lys Met Thr Cys Arg Gly Ser Asp Phe Glu Thr Ala Val Ala Arg Ala
                405                 410                 415 cag cgc gcg ttg gct gag ttc acc gtg tct ggt gtt gca acc aac att    1296
Gln Arg Ala Leu Ala Glu Phe Thr Val Ser Gly Val Ala Thr Asn Ile
                420                 425                 430 ggt ttc ttg cgt gcg ttg ctg cgt gaa gag gac ttt act tcc aag cgc    1344
Gly Phe Leu Arg Ala Leu Leu Arg Glu Glu Asp Phe Thr Ser Lys Arg
            435                 440                 445 atc gcc acc gga ttt atc ggc gat cac cca cac ctc ctt cag gct cca    1392
Ile Ala Thr Gly Phe Ile Gly Asp His Pro His Leu Leu Gln Ala Pro
        450                 455                 460 cct gcg gat gat gag cag gga cgc atc ctg gat tac ttg gca gat gtc    1440
Pro Ala Asp Asp Glu Gln Gly Arg Ile Leu Asp Tyr Leu Ala Asp Val
465                 470                 475                 480 acc gtg aac aag cct cat ggt gtg cgt cca aag gat gtt gca gca cca    1488
Thr Val Asn Lys Pro His Gly Val Arg Pro Lys Asp Val Ala Ala Pro
                485                 490                 495 atc gat aag ctg ccc aac atc aag gat ctg cca ctg cca cgc ggt tcc    1536
Ile Asp Lys Leu Pro Asn Ile Lys Asp Leu Pro Leu Pro Arg Gly Ser
                500                 505                 510 cgt gac cgc ctg aag cag ctt gga cca gca gcg ttt gcc cgc gat ctc    1584
Arg Asp Arg Leu Lys Gln Leu Gly Pro Ala Ala Phe Ala Arg Asp Leu
            515                 520                 525 cgt gag cag gac gca ctg gca gtt act gat acc acc ttc cgc gat gca    1632
Arg Glu Gln Asp Ala Leu Ala Val Thr Asp Thr Thr Phe Arg Asp Ala
530                 535                 540 cac cag tct ttg ctt gcg acc cga gtc cgc tca ttc gca ctg aag cct    1680
His Gln Ser Leu Leu Ala Thr Arg Val Arg Ser Phe Ala Leu Lys Pro
545                 550                 555                 560 gcg gca gag gcc gtc gca aag ctg act cct gag ctt ttg tcc gtg gag    1728
Ala Ala Glu Ala Val Ala Lys Leu Thr Pro Glu Leu Leu Ser Val Glu
                565                 570                 575 gcc tgg ggc ggt gcg acc tac gat gtg gcg atg cgt ttc ctc ttt gag    1776
Ala Trp Gly Gly Ala Thr Tyr Asp Val Ala Met Arg Phe Leu Phe Glu
                580                 585                 590 gat ccg tgg gac agg ctc gac gag ctg cgc gag gcg atg ccg aat gtg    1824
Asp Pro Trp Asp Arg Leu Asp Glu Leu Arg Glu Ala Met Pro Asn Val
            595                 600                 605 aac att cag atg ctg ctt cgc ggc cgc aac acc gtg gga tac acc cca    1872
Asn Ile Gln Met Leu Leu Arg Gly Arg Asn Thr Val Gly Tyr Thr Pro
        610                 615                 620 tac cca gac tcc gtc tgt cgc gcg ttt gtt aag gaa gct gcc acc tcc    1920
Tyr Pro Asp Ser Val Cys Arg Ala Phe Val Lys Glu Ala Ala Thr Ser
625                 630                 635                 640
```

| | |
|---|---|
| ggc gtg gac atc ttc cgc atc ttc gac gcg ctt aac gac gtc tcc cag<br>Gly Val Asp Ile Phe Arg Ile Phe Asp Ala Leu Asn Asp Val Ser Gln<br>645 650 655 | 1968 |
| atg cgt cca gca atc gac gca gtc ctg gag acc aac acc gcg gtc gct<br>Met Arg Pro Ala Ile Asp Ala Val Leu Glu Thr Asn Thr Ala Val Ala<br>660 665 670 | 2016 |
| gaa gtg gct atg gct tat tct ggt gat ctt tcc gat ccg aat gaa aag<br>Glu Val Ala Met Ala Tyr Ser Gly Asp Leu Ser Asp Pro Asn Glu Lys<br>675 680 685 | 2064 |
| ctc tac acc ctg gat tac tac ctg aag atg gca gag gag atc gtc aag<br>Leu Tyr Thr Leu Asp Tyr Tyr Leu Lys Met Ala Glu Glu Ile Val Lys<br>690 695 700 | 2112 |
| tct ggc gct cac att ctg gct att aag gat atg gct ggt ctg ctt cgc<br>Ser Gly Ala His Ile Leu Ala Ile Lys Asp Met Ala Gly Leu Leu Arg<br>705 710 715 720 | 2160 |
| cca gct gca gcc acc aag ctg gtc acc gca ctg cgc cgt gaa ttt gat<br>Pro Ala Ala Ala Thr Lys Leu Val Thr Ala Leu Arg Arg Glu Phe Asp<br>725 730 735 | 2208 |
| ctg cca gtg cac gtg cac acc cac gac act gcg ggt ggc cag ctg gca<br>Leu Pro Val His Val His Thr His Asp Thr Ala Gly Gly Gln Leu Ala<br>740 745 750 | 2256 |
| acc tac ttt gct gca gct caa gct ggt gca gat gct gtt gac ggt gct<br>Thr Tyr Phe Ala Ala Ala Gln Ala Gly Ala Asp Ala Val Asp Gly Ala<br>755 760 765 | 2304 |
| tcc gca cca ctg tct ggc acc acc tcc cag cca tcc ctg tct gcc att<br>Ser Ala Pro Leu Ser Gly Thr Thr Ser Gln Pro Ser Leu Ser Ala Ile<br>770 775 780 | 2352 |
| gtt gct gca ttc gcg cac acc cgt cgc gat acc ggt ttg agc ctc gag<br>Val Ala Ala Phe Ala His Thr Arg Arg Asp Thr Gly Leu Ser Leu Glu<br>785 790 795 800 | 2400 |
| gct gtt tct gac ctc gag cca tac tgg gaa gca gtg cgc gga ctg tac<br>Ala Val Ser Asp Leu Glu Pro Tyr Trp Glu Ala Val Arg Gly Leu Tyr<br>805 810 815 | 2448 |
| ctg cca ttt gag tct gga acc cca ggc cca acc ggt cgc gtc tac cgc<br>Leu Pro Phe Glu Ser Gly Thr Pro Gly Pro Thr Gly Arg Val Tyr Arg<br>820 825 830 | 2496 |
| cac gaa atc cca ggc gga cag ctg tcc aac ctg cgt gca cag gcc acc<br>His Glu Ile Pro Gly Gly Gln Leu Ser Asn Leu Arg Ala Gln Ala Thr<br>835 840 845 | 2544 |
| gca ctg ggc ctt gcg gat cgt ttc gaa ctc atc gaa gac aac tac gcg<br>Ala Leu Gly Leu Ala Asp Arg Phe Glu Leu Ile Glu Asp Asn Tyr Ala<br>850 855 860 | 2592 |
| gca gtt aat gag atg ctg gga cgc cca acc aag gtc acc cca tcc tcc<br>Ala Val Asn Glu Met Leu Gly Arg Pro Thr Lys Val Thr Pro Ser Ser<br>865 870 875 880 | 2640 |
| aag gtt gtt ggc gac ctc gca ctc cac ctc gtt ggt gcg ggt gtg gat<br>Lys Val Val Gly Asp Leu Ala Leu His Leu Val Gly Ala Gly Val Asp<br>885 890 895 | 2688 |
| cca gca gac ttt gct gca gat cca caa aag tac gac atc cca gac tct<br>Pro Ala Asp Phe Ala Ala Asp Pro Gln Lys Tyr Asp Ile Pro Asp Ser<br>900 905 910 | 2736 |
| gtc atc gcg ttc ctg cgc ggc gag ctt ggt aac cct cca ggt ggc tgg<br>Val Ile Ala Phe Leu Arg Gly Glu Leu Gly Asn Pro Pro Gly Gly Trp<br>915 920 925 | 2784 |
| cca gag cca ctg cgc acc cgc gca ctg gaa ggc cgc tcc gaa ggc aag<br>Pro Glu Pro Leu Arg Thr Arg Ala Leu Glu Gly Arg Ser Glu Gly Lys<br>930 935 940 | 2832 |
| gca cct ctg acg gaa gtt cct gag gaa gag cag gcg cac ctc gac gct<br>Ala Pro Leu Thr Glu Val Pro Glu Glu Glu Gln Ala His Leu Asp Ala | 2880 |

```
                 945                 950                 955                 960
gat gat tcc aag gaa cgt cgc aac agc ctc aac cgc ctg ctg ttc ccg        2928
Asp Asp Ser Lys Glu Arg Arg Asn Ser Leu Asn Arg Leu Leu Phe Pro
                965                 970                 975 aag cca acc gaa gag ttc ctc gag cac cgt cgc cgc ttc ggc aac acc        2976
Lys Pro Thr Glu Glu Phe Leu Glu His Arg Arg Arg Phe Gly Asn Thr
                980                 985                 990 tct gcg ctg gat gat cgt gaa ttc ttc tac ggc ctg gtc gaa ggc cgc        3024
Ser Ala Leu Asp Asp Arg Glu Phe Phe Tyr Gly Leu Val Glu Gly Arg
                995                 1000                1005 gag act ttg atc cgc ctg cca gat gtg cgc acc cca ctg ctt gtt            3069
Glu Thr Leu Ile Arg Leu Pro Asp Val Arg Thr Pro Leu Leu Val
        1010                1015                1020 cgc ctg gat gcg atc tcc gag cca gac gat aag ggt atg cgc aat            3114
Arg Leu Asp Ala Ile Ser Glu Pro Asp Asp Lys Gly Met Arg Asn
        1025                1030                1035 gtt gtg gcc aac gtc aac ggc cag atc cgc cca atg cgt gtg cgt            3159
Val Val Ala Asn Val Asn Gly Gln Ile Arg Pro Met Arg Val Arg
        1040                1045                1050 gac cgc tcc gtt gag tct gtc acc gca acc gca gaa aag gca gat            3204
Asp Arg Ser Val Glu Ser Val Thr Ala Thr Ala Glu Lys Ala Asp
        1055                1060                1065 tcc tcc aac aag ggc cat gtt gct gca cca ttc gct ggt gtt gtc            3249
Ser Ser Asn Lys Gly His Val Ala Ala Pro Phe Ala Gly Val Val
        1070                1075                1080 act gtg act gtt gct gaa ggt gat gag gtc aag gct gga gat gca            3294
Thr Val Thr Val Ala Glu Gly Asp Glu Val Lys Ala Gly Asp Ala
        1085                1090                1095 gtc gca atc atc gag gct atg aag atg gaa gca aca atc act gct            3339
Val Ala Ile Ile Glu Ala Met Lys Met Glu Ala Thr Ile Thr Ala
        1100                1105                1110 tct gtt gac ggc aaa atc gat cgc gtt gtg gtt cct gct gca acg            3384
Ser Val Asp Gly Lys Ile Asp Arg Val Val Val Pro Ala Ala Thr
        1115                1120                1125 aag gtg gaa ggt ggc gac ttg atc gtc gtc gtt tcc taa                    3423
Lys Val Glu Gly Gly Asp Leu Ile Val Val Val Ser
        1130                1135                1140

<210> SEQ ID NO 10
<211> LENGTH: 1140
<212> TYPE: PRT
<213> ORGANISM: Corynebacterium glutamicum

<400> SEQUENCE: 10

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110
```

```
Phe Ile Gly Pro Thr Pro Glu Val Leu Asp Leu Thr Gly Asp Lys Ser
            115                 120                 125
Arg Ala Val Thr Ala Ala Lys Lys Ala Gly Leu Pro Val Leu Ala Glu
        130                 135                 140
Ser Thr Pro Ser Lys Asn Ile Asp Asp Ile Val Lys Ser Ala Glu Gly
145                 150                 155                 160
Gln Thr Tyr Pro Ile Phe Val Lys Ala Val Ala Gly Gly Gly Gly Arg
                165                 170                 175
Gly Met Arg Phe Val Ser Ser Pro Asp Glu Leu Arg Lys Leu Ala Thr
            180                 185                 190
Glu Ala Ser Arg Glu Ala Glu Ala Phe Gly Asp Gly Ser Val Tyr
        195                 200                 205
Val Glu Arg Ala Val Ile Asn Pro Gln His Ile Glu Val Gln Ile Leu
210                 215                 220
Gly Asp Arg Thr Gly Glu Val Val His Leu Tyr Glu Arg Asp Cys Ser
225                 230                 235                 240
Leu Gln Arg Arg His Gln Lys Val Val Glu Ile Ala Pro Ala Gln His
                245                 250                 255
Leu Asp Pro Glu Leu Arg Asp Arg Ile Cys Ala Asp Ala Val Lys Phe
            260                 265                 270
Cys Arg Ser Ile Gly Tyr Gln Gly Ala Gly Thr Val Glu Phe Leu Val
        275                 280                 285
Asp Glu Lys Gly Asn His Val Phe Ile Glu Met Asn Pro Arg Ile Gln
        290                 295                 300
Val Glu His Thr Val Thr Glu Val Thr Glu Val Asp Leu Val Lys
305                 310                 315                 320
Ala Gln Met Arg Leu Ala Ala Gly Ala Thr Leu Lys Glu Leu Gly Leu
                325                 330                 335
Thr Gln Asp Lys Ile Lys Thr His Gly Ala Ala Leu Gln Cys Arg Ile
            340                 345                 350
Thr Thr Glu Asp Pro Asn Asn Gly Phe Arg Pro Asp Thr Gly Thr Ile
        355                 360                 365
Thr Ala Tyr Arg Ser Pro Gly Gly Ala Gly Val Arg Leu Asp Gly Ala
370                 375                 380
Ala Gln Leu Gly Gly Glu Ile Thr Ala His Phe Asp Ser Met Leu Val
385                 390                 395                 400
Lys Met Thr Cys Arg Gly Ser Asp Phe Glu Thr Ala Val Ala Arg Ala
                405                 410                 415
Gln Arg Ala Leu Ala Glu Phe Thr Val Ser Gly Val Ala Thr Asn Ile
            420                 425                 430
Gly Phe Leu Arg Ala Leu Leu Arg Glu Glu Asp Phe Thr Ser Lys Arg
        435                 440                 445
Ile Ala Thr Gly Phe Ile Gly Asp His Pro His Leu Leu Gln Ala Pro
450                 455                 460
Pro Ala Asp Asp Glu Gln Gly Arg Ile Leu Asp Tyr Leu Ala Asp Val
465                 470                 475                 480
Thr Val Asn Lys Pro His Gly Val Arg Pro Lys Asp Val Ala Ala Pro
                485                 490                 495
Ile Asp Lys Leu Pro Asn Ile Lys Asp Leu Pro Leu Pro Arg Gly Ser
            500                 505                 510
Arg Asp Arg Leu Lys Gln Leu Gly Pro Ala Ala Phe Ala Arg Asp Leu
        515                 520                 525
Arg Glu Gln Asp Ala Leu Ala Val Thr Asp Thr Thr Phe Arg Asp Ala
```

-continued

```
            530                 535                 540
His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
                580                 585                 590

Asp Pro Trp Asp Arg Leu Asp Glu Leu Arg Glu Ala Met Pro Asn Val
                595                 600                 605

Asn Ile Gln Met Leu Leu Arg Gly Arg Asn Thr Val Gly Tyr Thr Pro
                610                 615                 620

Tyr Pro Asp Ser Val Cys Arg Ala Phe Val Lys Glu Ala Ala Thr Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
                660                 665                 670

Glu Val Ala Met Ala Tyr Ser Gly Asp Leu Ser Asp Pro Asn Glu Lys
                675                 680                 685

Leu Tyr Thr Leu Asp Tyr Tyr Leu Lys Met Ala Glu Glu Ile Val Lys
                690                 695                 700

Ser Gly Ala His Ile Leu Ala Ile Lys Asp Met Ala Gly Leu Leu Arg
705                 710                 715                 720

Pro Ala Ala Ala Thr Lys Leu Val Thr Ala Leu Arg Arg Glu Phe Asp
                725                 730                 735

Leu Pro Val His Val His Thr His Asp Thr Ala Gly Gly Gln Leu Ala
                740                 745                 750

Thr Tyr Phe Ala Ala Gln Ala Gly Ala Asp Ala Val Asp Gly Ala
                755                 760                 765

Ser Ala Pro Leu Ser Gly Thr Thr Ser Gln Pro Ser Leu Ser Ala Ile
770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Pro Gly Pro Thr Gly Arg Val Tyr Arg
                820                 825                 830

His Glu Ile Pro Gly Gly Gln Leu Ser Asn Leu Arg Ala Gln Ala Thr
                835                 840                 845

Ala Leu Gly Leu Ala Asp Arg Phe Glu Leu Ile Glu Asp Asn Tyr Ala
850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
                900                 905                 910

Val Ile Ala Phe Leu Arg Gly Glu Leu Gly Asn Pro Pro Gly Gly Trp
                915                 920                 925

Pro Glu Pro Leu Arg Thr Arg Ala Leu Glu Gly Arg Ser Glu Gly Lys
                930                 935                 940

Ala Pro Leu Thr Glu Val Pro Glu Glu Glu Gln Ala His Leu Asp Ala
945                 950                 955                 960
```

```
Asp Asp Ser Lys Glu Arg Arg Asn Ser Leu Asn Arg Leu Leu Phe Pro
            965                 970                 975

Lys Pro Thr Glu Glu Phe Leu Glu His Arg Arg Arg Phe Gly Asn Thr
            980                 985                 990

Ser Ala Leu Asp Asp Arg Glu Phe Phe Tyr Gly Leu Val Glu Gly Arg
            995                 1000                1005

Glu Thr Leu Ile Arg Leu Pro Asp Val Arg Thr Pro Leu Leu Val
        1010                1015                1020

Arg Leu Asp Ala Ile Ser Glu Pro Asp Asp Lys Gly Met Arg Asn
        1025                1030                1035

Val Val Ala Asn Val Asn Gly Gln Ile Arg Pro Met Arg Val Arg
        1040                1045                1050

Asp Arg Ser Val Glu Ser Val Thr Ala Thr Ala Glu Lys Ala Asp
        1055                1060                1065

Ser Ser Asn Lys Gly His Val Ala Ala Pro Phe Ala Gly Val Val
        1070                1075                1080

Thr Val Thr Val Ala Glu Gly Asp Glu Val Lys Ala Gly Asp Ala
        1085                1090                1095

Val Ala Ile Ile Glu Ala Met Lys Met Glu Ala Thr Ile Thr Ala
        1100                1105                1110

Ser Val Asp Gly Lys Ile Asp Arg Val Val Val Pro Ala Ala Thr
        1115                1120                1125

Lys Val Glu Gly Gly Asp Leu Ile Val Val Val Ser
        1130                1135                1140

<210> SEQ ID NO 11
<211> LENGTH: 1626
<212> TYPE: DNA
<213> ORGANISM: Corynebacterium diphtheriae
<220> FEATURE:
<221> NAME/KEY: CDS
<222> LOCATION: (1)..(1626)

<400> SEQUENCE: 11 gtg gat atc

```
ccg gcc atg gct gcc gtg gtg gat tcg tta ccc agc atc ttt ggg gat      432
Pro Ala Met Ala Ala Val Val Asp Ser Leu Pro Ser Ile Phe Gly Asp
    130             135                 140 gcg aac aag gta cac gag gtg gaa tcg ttg ccc tta gtt gca tat tcg      480
Ala Asn Lys Val His Glu Val Glu Ser Leu Pro Leu Val Ala Tyr Ser
145             150                 155                 160 ctg gcc tac ccc atc ggc gta ttg gga gtt atc gcg gca att ggg ttg      528
Leu Ala Tyr Pro Ile Gly Val Leu Gly Val Ile Ala Ala Ile Gly Leu
                165                 170                 175 tgt gca aag tgg ttc cgt atc gat cac gtg caa gaa gct cac gac gca      576
Cys Ala Lys Trp Phe Arg Ile Asp His Val Gln Glu Ala His Asp Ala
            180                 185                 190 ggt gtt gct gtt gag gat ttg ttc acc cgt cag atc aag gtc aat cat      624
Gly Val Ala Val Glu Asp Leu Phe Thr Arg Gln Ile Lys Val Asn His
        195                 200                 205 gtg gtt acg ggc tct gat ctt gtg att gat atc cac cac acg ctg ggc      672
Val Val Thr Gly Ser Asp Leu Val Ile Asp Ile His His Thr Leu Gly
    210                 215                 220 cta gag att att gtc tcg cga att gag cgt gat ggt cag cag act ctc      720
Leu Glu Ile Ile Val Ser Arg Ile Glu Arg Asp Gly Gln Gln Thr Leu
225             230                 235                 240 cct act gcg tcg tct cgt atc cat atg gga gat gtg ttg tct gtg gtg      768
Pro Thr Ala Ser Ser Arg Ile His Met Gly Asp Val Leu Ser Val Val
                245                 250                 255 ggc acg gcc gag gaa ctc gac aag gcc gcg cat gtg cta ggt gat ttg      816
Gly Thr Ala Glu Glu Leu Asp Lys Ala Ala His Val Leu Gly Asp Leu
            260                 265                 270 ctc cca ggc gat cct ttc cat ggt cac gat tta gat tat cgg cgc att      864
Leu Pro Gly Asp Pro Phe His Gly His Asp Leu Asp Tyr Arg Arg Ile
        275                 280                 285 ttt gtt tcc aat cag gat tta gtg ggc ata cct ctg gct aaa ctt cgg      912
Phe Val Ser Asn Gln Asp Leu Val Gly Ile Pro Leu Ala Lys Leu Arg
    290                 295                 300 cct cga ttg tca gga att ttg att act cgg gtc cgt cgt ggc gac cat      960
Pro Arg Leu Ser Gly Ile Leu Ile Thr Arg Val Arg Arg Gly Asp His
305             310                 315                 320 gac cat gtg gct act ccg gaa aca gtt ttg cag ctt ggc gac cgt gtt     1008
Asp His Val Ala Thr Pro Glu Thr Val Leu Gln Leu Gly Asp Arg Val
                325                 330                 335 cgg gtg gtg gca gct cat gat cgt atg aaa tcc gtg acg gca ctg ttc     1056
Arg Val Val Ala Ala His Asp Arg Met Lys Ser Val Thr Ala Leu Phe
            340                 345                 350 ggc gat tcc tat cgt cgc ctt tct gat ttc aat ctt ttc cct ctc gtt     1104
Gly Asp Ser Tyr Arg Arg Leu Ser Asp Phe Asn Leu Phe Pro Leu Val
        355                 360                 365 gcc ggg ctt gcg ctt gga ttg ctc gtt ggc atg att gag gta cca ctt     1152
Ala Gly Leu Ala Leu Gly Leu Leu Val Gly Met Ile Glu Val Pro Leu
    370                 375                 380 cct ggc ggt gct gcg ttg tct tta gga agc gcc ggc ggc cca tta gta     1200
Pro Gly Gly Ala Ala Leu Ser Leu Gly Ser Ala Gly Gly Pro Leu Val
385             390                 395                 400 gta gct ctc gtt cta ggc gca gtg gga cgc tca ggt cgt ttt gtg tgg     1248
Val Ala Leu Val Leu Gly Ala Val Gly Arg Ser Gly Arg Phe Val Trp
                405                 410                 415 cag gtt cct tac gga gca aac ttg gca ctg cga caa cta ggc atc acc     1296
Gln Val Pro Tyr Gly Ala Asn Leu Ala Leu Arg Gln Leu Gly Ile Thr
            420                 425                 430 ttg ttt ctc gcc gct att ggt acc act gca gga gct agt ttc cgt gca     1344
Leu Phe Leu Ala Ala Ile Gly Thr Thr Ala Gly Ala Ser Phe Arg Ala
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
|     |     |     | 435 |     |     |     |     | 440 |     |     |     |     | 445 |     |     |      |
| tcg | cta | tca | gat | ccc | gca | tcg | ttg | acc | atc | att | gcc | gtt | ggt | gcc | atc | 1392 |
| Ser | Leu | Ser | Asp | Pro | Ala | Ser | Leu | Thr | Ile | Ile | Ala | Val | Gly | Ala | Ile |      |
|     | 450 |     |     |     |     | 455 |     |     |     |     | 460 |     |     |     |     |      |
| atc | acc | ttg | aca | ttg | gct | atc | ttt | gtt | ctg | gtt | gtg | ggc | tat | aag | gtg | 1440 |
| Ile | Thr | Leu | Thr | Leu | Ala | Ile | Phe | Val | Leu | Val | Val | Gly | Tyr | Lys | Val |      |
| 465 |     |     |     |     | 470 |     |     |     |     | 475 |     |     |     |     | 480 |      |
| atg | aag | atc | ccg | tac | ggc | caa | aca | gcg | ggc | atg | ctt | gcg | ggt | att | caa | 1488 |
| Met | Lys | Ile | Pro | Tyr | Gly | Gln | Thr | Ala | Gly | Met | Leu | Ala | Gly | Ile | Gln |      |
|     |     |     |     | 485 |     |     |     |     | 490 |     |     |     |     | 495 |     |      |
| acg | cac | cca | gct | gta | ctg | tcc | tat | gtt | tct | gcg | atg | acg | aaa | aat | gat | 1536 |
| Thr | His | Pro | Ala | Val | Leu | Ser | Tyr | Val | Ser | Ala | Met | Thr | Lys | Asn | Asp |      |
|     |     |     | 500 |     |     |     |     | 505 |     |     |     |     | 510 |     |     |      |
| ctg | ccg | gca | ttg | ggc | tac | acc | tcg | gta | tat | cca | ctg | gcc | atg | atc | gct | 1584 |
| Leu | Pro | Ala | Leu | Gly | Tyr | Thr | Ser | Val | Tyr | Pro | Leu | Ala | Met | Ile | Ala |      |
|     |     | 515 |     |     |     |     | 520 |     |     |     |     | 525 |     |     |     |      |
| aag | atc | att | gca | gca | cag | gtt | gtg | cta | ttc | gct | ttg | aca | tag |     |     | 1626 |
| Lys | Ile | Ile | Ala | Ala | Gln | Val | Val | Leu | Phe | Ala | Leu | Thr |     |     |     |      |
| 530 |     |     |     |     | 535 |     |     |     |     | 540 |     |     |     |     |     |      |

<210> SEQ ID NO 12
<211> LENGTH: 541
<212> TYPE: PRT
<213> ORGANISM: Corynebacterium diphtheriae

<400> SEQUENCE: 12

Met Asp Ile Phe Val Ala Asn Pro Leu Leu Ala Leu Phe Val Ile Met
1               5                   10                  15

Ala Val Gly Leu Ala Ile Gly Gln Val Lys Ile Arg Gly Phe Ser Leu
            20                  25                  30

Gly Val Ala Ala Val Leu Phe Ala Gly Val Gly Phe Ala Ala Val Glu
        35                  40                  45

Pro Asp Ile His Ile Pro His Leu Val Tyr Ile Leu Gly Leu Ser Ile
    50                  55                  60

Phe Val Tyr Ser Ile Gly Leu Glu Ser Gly His Ala Phe Phe Ala Leu
65                  70                  75                  80

Phe Lys Ser Gln Gly Val Lys Gln Asn Ala Leu Ala Ile Thr Ala Leu
                85                  90                  95

Ala Leu Ile Thr Gly Ile Ser Ile Ala Leu Phe Ser Leu Ile His Leu
            100                 105                 110

Asn Gly Val Thr Ala Ala Gly Leu Phe Thr Gly Ala Val Thr Asn Thr
        115                 120                 125

Pro Ala Met Ala Ala Val Val Asp Ser Leu Pro Ser Ile Phe Gly Asp
    130                 135                 140

Ala Asn Lys Val His Glu Val Glu Ser Leu Pro Leu Val Ala Tyr Ser
145                 150                 155                 160

Leu Ala Tyr Pro Ile Gly Val Leu Gly Val Ile Ala Ala Ile Gly Leu
                165                 170                 175

Cys Ala Lys Trp Phe Arg Ile Asp His Val Gln Glu Ala His Asp Ala
            180                 185                 190

Gly Val Ala Val Glu Asp Leu Phe Thr Arg Gln Ile Lys Val Asn His
        195                 200                 205

Val Val Thr Gly Ser Asp Leu Val Ile Asp Ile His His Thr Leu Gly
    210                 215                 220

Leu Glu Ile Ile Val Ser Arg Ile Glu Arg Asp Gly Gln Gln Thr Leu
225                 230                 235                 240

```
Pro Thr Ala Ser Ser Arg Ile His Met Gly Asp Val Leu Ser Val Val
                245                 250                 255

Gly Thr Ala Glu Glu Leu Asp Lys Ala Ala His Val Leu Gly Asp Leu
            260                 265                 270

Leu Pro Gly Asp Pro Phe His Gly His Asp Leu Asp Tyr Arg Arg Ile
        275                 280                 285

Phe Val Ser Asn Gln Asp Leu Val Gly Ile Pro Leu Ala Lys Leu Arg
    290                 295                 300

Pro Arg Leu Ser Gly Ile Leu Ile Thr Arg Val Arg Gly Asp His
305                 310                 315                 320

Asp His Val Ala Thr Pro Glu Thr Val Leu Gln Leu Gly Asp Arg Val
                325                 330                 335

Arg Val Val Ala Ala His Asp Arg Met Lys Ser Val Thr Ala Leu Phe
            340                 345                 350

Gly Asp Ser Tyr Arg Arg Leu Ser Asp Phe Asn Leu Phe Pro Leu Val
        355                 360                 365

Ala Gly Leu Ala Leu Gly Leu Val Gly Met Ile Glu Val Pro Leu
    370                 375                 380

Pro Gly Gly Ala Ala Leu Ser Leu Gly Ser Ala Gly Gly Pro Leu Val
385                 390                 395                 400

Val Ala Leu Val Leu Gly Ala Val Gly Arg Ser Gly Arg Phe Val Trp
                405                 410                 415

Gln Val Pro Tyr Gly Ala Asn Leu Ala Leu Arg Gln Leu Gly Ile Thr
            420                 425                 430

Leu Phe Leu Ala Ala Ile Gly Thr Thr Ala Gly Ala Ser Phe Arg Ala
        435                 440                 445

Ser Leu Ser Asp Pro Ala Ser Leu Thr Ile Ile Ala Val Gly Ala Ile
    450                 455                 460

Ile Thr Leu Thr Leu Ala Ile Phe Val Leu Val Val Gly Tyr Lys Val
465                 470                 475                 480

Met Lys Ile Pro Tyr Gly Gln Thr Ala Gly Met Leu Ala Gly Ile Gln
                485                 490                 495

Thr His Pro Ala Val Leu Ser Tyr Val Ser Ala Met Thr Lys Asn Asp
            500                 505                 510

Leu Pro Ala Leu Gly Tyr Thr Ser Val Tyr Pro Leu Ala Met Ile Ala
        515                 520                 525

Lys Ile Ile Ala Ala Gln Val Val Leu Phe Ala Leu Thr
    530                 535                 540

<210> SEQ ID NO 13
<211> LENGTH: 1502
<212> TYPE: DNA
<213> ORGANISM: Brevibacterium flavum
<220> FEATURE:
<221> NAME/KEY: CDS
<222> LOCATION: (301)..(1287)

<400> SEQUENCE: 13
cctttcgggt aacgagaaaa cgtgaactag aaacggagtc aaagtaaata tcaaaggtaa      60
caccatcggt aaatccaaac tgacaactat aaatggtgcc cgatatcagg aaaaattgct     120
tgcacaccgc gccgattccc catgatgccc taacatcttg caggtaaggg gtacatattg     180
gggcaattcg ggggtgattt tgcagtatcg tcaagatcac ccaaaactgg tgctgttct      240 cttttaagcg ggatagcatg ggttcttaga ggacccccta caaggattga ggattgttta     300 atg aat tcc ccg cag aac gtc tcc acc aag aag gtc acc gtc acc ggc      348
```

```
Met Asn Ser Pro Gln Asn Val Ser Thr Lys Lys Val Thr Val Thr Gly
1               5                   10                  15 gca gct ggt caa atc tct tat tca ctg ttg tgg cgc atc gct aac ggt      396
Ala Ala Gly Gln Ile Ser Tyr Ser Leu Leu Trp Arg Ile Ala Asn Gly
            20                  25                  30 gaa gta ttc ggc act gaa acc cct gtt gag ctg aag ctg ctg gaa atc      444
Glu Val Phe Gly Thr Glu Thr Pro Val Glu Leu Lys Leu Leu Glu Ile
                35                  40                  45 cct cag gca ctt ggt ggg gca gag ggc gtg gcc atg gaa ctt ctt gat      492
Pro Gln Ala Leu Gly Gly Ala Glu Gly Val Ala Met Glu Leu Leu Asp
        50                  55                  60 tca gcc ttc cca ctc ctg cga aac atc acc atc acc gcc gat gcc aat      540
Ser Ala Phe Pro Leu Leu Arg Asn Ile Thr Ile Thr Ala Asp Ala Asn
65                  70                  75                  80 gag gca ttc gac ggc gct aat gcg gcg ttt ttg gtc ggt gcg aag cct      588
Glu Ala Phe Asp Gly Ala Asn Ala Ala Phe Leu Val Gly Ala Lys Pro
                85                  90                  95 cgc gga aaa ggc gaa gag cgc gca gat ctg ctg gct aac aac ggc aag      636
Arg Gly Lys Gly Glu Glu Arg Ala Asp Leu Leu Ala Asn Asn Gly Lys
            100                 105                 110 att ttc gga cct caa ggt aaa gct atc aat gac aac gcc gca gat gac      684
Ile Phe Gly Pro Gln Gly Lys Ala Ile Asn Asp Asn Ala Ala Asp Asp
        115                 120                 125 att cgt gtc cta gtt gtt gga aac cca gcg aac acc aac gcg ttg att      732
Ile Arg Val Leu Val Val Gly Asn Pro Ala Asn Thr Asn Ala Leu Ile
130                 135                 140 gct tca gct gcg gcc cca gat gtt cca gca tcc cgc ttc aac gca atg      780
Ala Ser Ala Ala Ala Pro Asp Val Pro Ala Ser Arg Phe Asn Ala Met
145                 150                 155                 160 atg cgc ctt gat cac aac cgt gcg atc tcc cag ctg gcc acc aag ctt      828
Met Arg Leu Asp His Asn Arg Ala Ile Ser Gln Leu Ala Thr Lys Leu
                165                 170                 175 ggc cgt gga tct gcg gaa ttt aac aac att gtg gtc tgg gga aat cac      876
Gly Arg Gly Ser Ala Glu Phe Asn Asn Ile Val Val Trp Gly Asn His
            180                 185                 190 tcc gca acc cag ttc cca gac atc acc tac gca acc gtt ggt gga gaa      924
Ser Ala Thr Gln Phe Pro Asp Ile Thr Tyr Ala Thr Val Gly Gly Glu
        195                 200                 205 aag gtc acc gac ctg gtt gat cac gat tgg tat gtg gag gag ttc att      972
Lys Val Thr Asp Leu Val Asp His Asp Trp Tyr Val Glu Glu Phe Ile
210                 215                 220 cct cgc gtg gct aac cgt ggc gct gaa atc att gag gtc cgt gga aag     1020
Pro Arg Val Ala Asn Arg Gly Ala Glu Ile Ile Glu Val Arg Gly Lys
225                 230                 235                 240 tct tct gca gct tct gca gca tcc tct gcg att gat cac atg cgc gat     1068
Ser Ser Ala Ala Ser Ala Ala Ser Ser Ala Ile Asp His Met Arg Asp
                245                 250                 255 tgg gta cag ggc acc gag gcg tgg tcc tct gcg gca att cct tcc acc     1116
Trp Val Gln Gly Thr Glu Ala Trp Ser Ser Ala Ala Ile Pro Ser Thr
            260                 265                 270 ggt gca tac ggc att cct gag ggc att ttt gtc ggt ctg cca acc gta     1164
Gly Ala Tyr Gly Ile Pro Glu Gly Ile Phe Val Gly Leu Pro Thr Val
        275                 280                 285 tcc cgc aac ggt gag tgg gaa atc gtt gaa ggc ctg gag att tcc gat     1212
Ser Arg Asn Gly Glu Trp Glu Ile Val Glu Gly Leu Glu Ile Ser Asp
290                 295                 300 ttc cag cgc gcc cgc atc gac gcg aat gct cag gaa ttg cag gcc gag     1260
Phe Gln Arg Ala Arg Ile Asp Ala Asn Ala Gln Glu Leu Gln Ala Glu
305                 310                 315                 320
```

```
cgc gag gca gtg cgc gac ttg ctc taa tctttaacgc atgacttcgc         1307
Arg Glu Ala Val Arg Asp Leu Leu
                325 ttttcgacgc cccaaccctc caacgcgtca ccgttttcac gggctcggcg ctcggcagtt   1367 cctcgctgta cacgcaagcg gctcaaacct tggcgaaaac cgcggtagac cgcggcatcg   1427 acttggttta cggtggcgga aaagtggggc tcatgggtat cgtcgcggat gcgttcctgg   1487 aatcaggtgg cgaag                                                   1502

<210> SEQ ID NO 14
<211> LENGTH: 328
<212> TYPE: PRT
<213> ORGANISM: Brevibacterium flavum

<400> SEQUENCE: 14

Met Asn Ser Pro Gln Asn Val Ser Thr Lys Lys Val Thr Val Thr Gly
1               5                   10                  15

Ala Ala Gly Gln Ile Ser Tyr Ser Leu Leu Trp Arg Ile Ala Asn Gly
                20                  25                  30

Glu Val Phe Gly Thr Glu Thr Pro Val Glu Leu Lys Leu Leu Glu Ile
            35                  40                  45

Pro Gln Ala Leu Gly Gly Ala Glu Gly Val Ala Met Glu Leu Leu Asp
        50                  55                  60

Ser Ala Phe Pro Leu Leu Arg Asn Ile Thr Ile Thr Ala Asp Ala Asn
65                  70                  75                  80

Glu Ala Phe Asp Gly Ala Asn Ala Ala Phe Leu Val Gly Ala Lys Pro
                85                  90                  95

Arg Gly Lys Gly Glu Glu Arg Ala Asp Leu Leu Ala Asn Asn Gly Lys
            100                 105                 110

Ile Phe Gly Pro Gln Gly Lys Ala Ile Asn Asp Asn Ala Ala Asp Asp
        115                 120                 125

Ile Arg Val Leu Val Val Gly Asn Pro Ala Asn Thr Asn Ala Leu Ile
130                 135                 140

Ala Ser Ala Ala Ala Pro Asp Val Pro Ala Ser Arg Phe Asn Ala Met
145                 150                 155                 160

Met Arg Leu Asp His Asn Arg Ala Ile Ser Gln Leu Ala Thr Lys Leu
                165                 170                 175

Gly Arg Gly Ser Ala Glu Phe Asn Asn Ile Val Val Trp Gly Asn His
            180                 185                 190

Ser Ala Thr Gln Phe Pro Asp Ile Thr Tyr Ala Thr Val Gly Gly Glu
        195                 200                 205

Lys Val Thr Asp Leu Val Asp His Asp Trp Tyr Val Glu Glu Phe Ile
    210                 215                 220

Pro Arg Val Ala Asn Arg Gly Ala Glu Ile Ile Glu Val Arg Gly Lys
225                 230                 235                 240

Ser Ser Ala Ala Ser Ala Ala Ser Ser Ala Ile Asp His Met Arg Asp
                245                 250                 255

Trp Val Gln Gly Thr Glu Ala Trp Ser Ser Ala Ala Ile Pro Ser Thr
            260                 265                 270

Gly Ala Tyr Gly Ile Pro Glu Gly Ile Phe Val Gly Leu Pro Thr Val
        275                 280                 285

Ser Arg Asn Gly Glu Trp Glu Ile Val Glu Gly Leu Glu Ile Ser Asp
    290                 295                 300

Phe Gln Arg Ala Arg Ile Asp Ala Asn Ala Gln Glu Leu Gln Ala Glu
305                 310                 315                 320
```

Arg Glu Ala Val Arg Asp Leu Leu
                325

<210> SEQ ID NO 15
<211> LENGTH: 32
<212> TYPE: DNA
<213> ORGANISM: Artificial
<220> FEATURE:
<223> OTHER INFORMATION: primer

<400> SEQUENCE: 15
gggaaggatc cctttcggg taacgagaaa ac                                      32

<210> SEQ ID NO 16
<211> LENGTH: 31
<212> TYPE: DNA
<213> ORGANISM: Artificial
<220> FEATURE:
<223> OTHER INFORMATION: primer

<400> SEQUENCE: 16
gggaaggatc ccttcgccac ctgattccag g                                      31

<210> SEQ ID NO 17
<211> LENGTH: 33
<212> TYPE: DNA
<213> ORGANISM: Artificial
<220> FEATURE:
<223> OTHER INFORMATION: primer

<400> SEQUENCE: 17
gggcctgcag gaccaagacc gctgttgcag tga                                    33

<210> SEQ ID NO 18
<211> LENGTH: 31
<212> TYPE: DNA
<213> ORGANISM: Artificial
<220> FEATURE:
<223> OTHER INFORMATION: primer

<400> SEQUENCE: 18
gggcctgcag ggtattcaca ccagccccaa t                                      31

<210> SEQ ID NO 19
<211> LENGTH: 40
<212> TYPE: DNA
<213> ORGANISM: Artificial
<220> FEATURE:
<223> OTHER INFORMATION: primer

<400> SEQUENCE: 19
tcgcttttta ggagcacccc gtgagcttcc ttgtagaaaa                              40

<210> SEQ ID NO 20
<211> LENGTH: 20
<212> TYPE: DNA
<213> ORGANISM: Artificial
<220> FEATURE:
<223> OTHER INFORMATION: primer

<400> SEQUENCE: 20
ccaaggtcag tgcgttgttg                                                   20

<210> SEQ ID NO 21
<211> LENGTH: 29

<212> TYPE: DNA
<213> ORGANISM: Artificial
<220> FEATURE:
<223> OTHER INFORMATION: primer

<400> SEQUENCE: 21
ggtctagaag ttcgccgacg gaatccacg                                              29

<210> SEQ ID NO 22
<211> LENGTH: 40
<212> TYPE: DNA
<213> ORGANISM: Artificial
<220> FEATURE:
<223> OTHER INFORMATION: primer

<400> SEQUENCE: 22
ttttctacaa ggaagctcac ggggtgctcc taaaaagcga                                  40

<210> SEQ ID NO 23
<211> LENGTH: 27
<212> TYPE: DNA
<213> ORGANISM: Artificial
<220> FEATURE:
<223> OTHER INFORMATION: primer

<400> SEQUENCE: 23
ggtctagacg atcaattcct ttcgggt                                                27

<210> SEQ ID NO 24
<211> LENGTH: 30
<212> TYPE: DNA
<213> ORGANISM: Artificial
<220> FEATURE:
<223> OTHER INFORMATION: primer

<400> SEQUENCE: 24
ggcctgcagg gcgttaaaga ttagagcaag                                             30

<210> SEQ ID NO 25
<211> LENGTH: 40
<212> TYPE: DNA
<213> ORGANISM: Artificial
<220> FEATURE:
<223> OTHER INFORMATION: primer

<400> SEQUENCE: 25
gaagtccagg aggacataca atgaattccc cgcagaacgt                                  40

<210> SEQ ID NO 26
<211> LENGTH: 20
<212> TYPE: DNA
<213> ORGANISM: Artificial
<220> FEATURE:
<223> OTHER INFORMATION: primer

<400> SEQUENCE: 26
tcattgcgtt gaagcgggat                                                        20

<210> SEQ ID NO 27
<211> LENGTH: 29
<212> TYPE: DNA
<213> ORGANISM: Artificial
<220> FEATURE:
<223> OTHER INFORMATION: primer

<400> SEQUENCE: 27

```
ggggatccag atcgtttaga tccgaagga                                          29
```

<210> SEQ ID NO 28
<211> LENGTH: 40
<212> TYPE: DNA
<213> ORGANISM: Artificial
<220> FEATURE:
<223> OTHER INFORMATION: primer

<400> SEQUENCE: 28

```
acgttctgcg gggaattcat tgtatgtcct cctggacttc                              40
```

<210> SEQ ID NO 29
<211> LENGTH: 30
<212> TYPE: DNA
<213> ORGANISM: Artificial
<220> FEATURE:
<223> OTHER INFORMATION: primer

<400> SEQUENCE: 29

```
ggcctgcagg gcgttaaaga ttagagcaag                                         30
```

<210> SEQ ID NO 30
<211> LENGTH: 28
<212> TYPE: DNA
<213> ORGANISM: Artificial
<220> FEATURE:
<223> OTHER INFORMATION: primer

<400> SEQUENCE: 30

```
ggactagtag atcgtttaga tccgaagg                                           28
```

<210> SEQ ID NO 31
<211> LENGTH: 20
<212> TYPE: DNA
<213> ORGANISM: Artificial
<220> FEATURE:
<223> OTHER INFORMATION: primer

<400> SEQUENCE: 31

```
cactgcacgg ccctgcgaac                                                    20
```

<210> SEQ ID NO 32
<211> LENGTH: 42
<212> TYPE: DNA
<213> ORGANISM: Artificial
<220> FEATURE:
<223> OTHER INFORMATION: primer

<400> SEQUENCE: 32

```
cgccaactag gcgccaaaaa ttcctgattt ccctaaccgg ac                           42
```

<210> SEQ ID NO 33
<211> LENGTH: 42
<212> TYPE: DNA
<213> ORGANISM: Artificial
<220> FEATURE:
<223> OTHER INFORMATION: primer

<400> SEQUENCE: 33

```
gtccggttag ggaaatcagg aattttttggc gcctagttgg cg                          42
```

<210> SEQ ID NO 34
<211> LENGTH: 20
<212> TYPE: DNA
<213> ORGANISM: Artificial

```
<220> FEATURE:
<223> OTHER INFORMATION: primer

<400> SEQUENCE: 34
tgtgggcctt cggcgaggac                                                  20

<210> SEQ ID NO 35
<211> LENGTH: 26
<212> TYPE: DNA
<213> ORGANISM: Artificial
<220> FEATURE:
<223> OTHER INFORMATION: primer

<400> SEQUENCE: 35
gagtcgaccg caccccattt ttcata                                           26

<210> SEQ ID NO 36
<211> LENGTH: 28
<212> TYPE: DNA
<213> ORGANISM: Artificial
<220> FEATURE:
<223> OTHER INFORMATION: primer

<400> SEQUENCE: 36
tggtcgacgt gaatgctcgg cgggatcc                                         28

<210> SEQ ID NO 37
<211> LENGTH: 300
<212> TYPE: DNA
<213> ORGANISM: Corynebacterium glutamicum

<400> SEQUENCE: 37
aagcgcctca tcagcggtaa ccatcacggg ttcgggtgcg aaaaaccatg ccataacagg       60
aatgttcctt tcgaaaattg aggaagcctt atgcccttca accctactta gctgccaatt      120
attccgggct tgtgacccgc tacccgataa ataggtcggc tgaaaaattt cgttgcaata      180
tcaacaaaaa ggcctatcat tgggaggtgt cgcaccaagt acttttgcga agcgccatct      240
gacggatttt caaaagatgt atatgctcgg tgcggaaacc tacgaaagga ttttttaccc      300

<210> SEQ ID NO 38
<211> LENGTH: 299
<212> TYPE: DNA
<213> ORGANISM: Corynebacterium glutamicum

<400> SEQUENCE: 38
gcggcccggg ttggcggcct gcccatcgca gtcgcggaag gggagacggg attgcttgtc       60
gacggccact ccccgcatgc ctgggccgac gccttagcca cactcttgga cgatgacgaa      120
acgcgcatca gaatgggtga agacgccgtc gaacacgcca gaacattctc ctgggcggcc      180
accgccgcac agctatcgtc gctgtacaac gacgctattg ccaacgaaaa tgtcgacggt      240
gaaacgcatc acggctaagt aaacgcgcgt cgtggaacat aaagtggcaa actagtacc      299

<210> SEQ ID NO 39
<211> LENGTH: 285
<212> TYPE: DNA
<213> ORGANISM: Corynebacterium glutamicum

<400> SEQUENCE: 39
gcgaagacat cacgttggat gaaattgagc gaattaagga cggcattcgc gccgctcgta       60
actaccgcga tgattatcca gaggaattca acctgtggcg caacgctgta tataacctgc      120
```

```
gtacggctta aagtttggct gccatgtgaa ttttagcac cctcaacagt tgagtgctgg      180
cactctcggg ggtagagtgc caaataggtt gtttgacaca cagttgttca cccgcgacga      240
cggctgtgct ggaaacccac aaccggcaca cacaaaattt ttctc                     285
```

<210> SEQ ID NO 40
<211> LENGTH: 300
<212> TYPE: DNA
<213> ORGANISM: Corynebacterium glutamicum
<400> SEQUENCE: 40

```
atcgacggca tgaaaccttg cacaaaagtg ctataggttt cgttgatcaa ccggcgtgat       60
tccgcagcaa ttgtgccgaa caccagcgag gacttgccag atcccgacac acccgtgaac      120
acggtgagac gccttttagg gatgcgcacc gacacatttt tgaggttgtt ttcattcgca      180
ccgtggaccg aaatccaatc atgggaatca gcttttttgca tgtgtcatat cgtaccgttt     240
gcataggcct gttcgcgctt ggtgaacctt ttctagcacc aaaacaaaac tctccctagt     300
```

<210> SEQ ID NO 41
<211> LENGTH: 300
<212> TYPE: DNA
<213> ORGANISM: Corynebacterium glutamicum
<400> SEQUENCE: 41

```
gatagttcaa accgccaggc aacttcactg agattccacc acgcgaatta atagtcaccg       60
gcccgattcg cttcgatccg gaaacgccag acttagaaac attcagccaa ctgtcttttc     120
cggtcttaat aattttccga taattcagtc ccatgtgaac cagcataatc ttcatcacat     180
ggtgtgtgca gaaatatttt tgctggtcta ttgtggcgac cgagggcctt tgaaggttcg     240
acaaactgta taaggccttg aatcttgaga atttattttg aggaagcaag aggaagtgtc     300
```

<210> SEQ ID NO 42
<211> LENGTH: 300
<212> TYPE: DNA
<213> ORGANISM: Corynebacterium glutamicum
<400> SEQUENCE: 42

```
actatttagc gcaagtgttg gaaatgcccc cgtttggggt caatgtccat ttttgaatgt       60
gtctgtatga ttttgcatct gctgcgaaat ctttgtttcc ccgctaaagt tgaggacagg     120
ttgacacgga gttgactcga cgaattatcc aatgtgagta ggtttggtgc gtgagttgga     180
aaaattcgcc atactcgccc ttgggttctg tcagctcaag aattcttgag tgaccgatgc     240
tctgattgac ctaactgctt gacacattgc atttcctaca atctttagag gagacacaac    300
```

<210> SEQ ID NO 43
<211> LENGTH: 300
<212> TYPE: DNA
<213> ORGANISM: Corynebacterium glutamicum
<400> SEQUENCE: 43

```
tcgccgcggg tgaggtggcc ttcggatgcg atgagggctg cgtcgatgtt gatttctgaa       60
aaatcgttga caatgactgc gattttccgg gatcctcgt ggtggaggat ctggttgagc     120
aatgtggttt ttccggagcc gagaaatcct gatagcacgg tgactggggt cgttgtggcc     180
atgtgaaagc cctcctttg ggaatcattt tcaatagagt cgacgcaagt gtacacttct     240
taatggaaat tgttttcaat aaagtcaagt ttttgacct tcgcttttta ggagcacccc     300
```

```
<210> SEQ ID NO 44
<211> LENGTH: 300
<212> TYPE: DNA
<213> ORGANISM: Corynebacterium glutamicum

<400> SEQUENCE: 44
tggccgaaga actggaaaac aacggcaata gttacaccgg tcgctcccga tagccccgat        60
agtgtatgtg ctgacctgcg tttatgcatt ttccttaggt tgaaggaaat atcacacgac       120
aaaagttgag tgatgcaggc ataattggct ataggcaact gaagatgcca caatcaatgt       180
ttgatccaac agaatcagac attgtgaatg tgggattatc ggttcgcgct tcaccatgtt       240
tctgcatgat gaaattacat acatagttca gtgacagtca cctttggag gagacaccatt       300

<210> SEQ ID NO 45
<211> LENGTH: 300
<212> TYPE: DNA
<213> ORGANISM: Brevibacgterium flavum

<400> SEQUENCE: 45
gcgttttagc gtgtcagtag gcgcgtaggg taagtggggt agcggcttgt tagatatctt        60
gaaatcggct ttcaacagca ttgatttcga tgtatttagc tggccgttac cctgcgaatg       120
tccacagggt agctggtagt ttgaaaatca acgccgttgc ccttaggatt cagtaactgg       180
cacattttgt aatgcgctag atctgtgtgc tcagtcttcc aggctgctga tcacagtgaa       240
agcaaaacca attcgtggct gcgaaagtcg tagccaccac gaagtccagg aggacataca       300
```

METHOD FOR PRODUCING AN ORGANIC ACID

This application is a continuation under 35 U.S.C. §120 of PCT Patent Application No. PCT/JP2008/057086, filed Apr. 10, 2008, which claims priority under 35 U.S.C. §119 to Japanese Patent Application No. 2007-102668, filed on Apr. 10, 2007, which are incorporated in their entireties by reference. The Sequence Listing in electronic format filed herewith is also hereby incorporated by reference in its entirety (File Name: US-410_Seq_List; File Size: 91 KB; Date Created: Oct. 9, 2009).

BACKGROUND OF THE INVENTION

1. Technical Field

The present invention relates to a method for producing an organic acid using a bacterium such as a coryneform bacterium.

2. Background Art

For the production of non-amino organic acids, including succinic acid, by fermentation, anaerobic bacteria are typically used, including anaerobic bacteria belonging to the genus *Anaerobiospirillum* or *Actinobacillus* (U.S. Pat. No. 5,142,834, International Journal of Systematic Bacteriology, 49, 207-216 (1999)). Although such anaerobic bacteria provide high yields of products, many nutrients are required for their proliferation, and therefore it is necessary to add large amounts of organic nitrogen sources such as corn steep liquor (CSL) into the culture medium. The addition of large amounts of sources of organic nitrogen results in not only an increase in cost for the culture medium, but also an increase in the purification costs for isolating the product, and therefore it is not economical.

In addition, methods are known in which aerobic bacteria such as coryneform bacteria are cultured once under aerobic conditions to proliferate the bacterial cells, then the cells are harvested, washed, and allowed to rest so that a non-amino organic acid is produced without having to supply oxygen (Japanese Patent Laid-open (KOKAI) Nos. 11-113588 and 11-196888). When aerobic bacteria which were grown under aerobic conditions are used for the production of non-amino organic acids as described above, a culture under microaerobic conditions (also called "microaerobic induction") is generally necessary to produce succinic acid under anaerobic conditions. These methods are economical, since organic nitrogen can be added in a smaller amount for proliferation of the bacterial cells, and the bacteria can sufficiently grow in a simple culture medium. However, there is still a room for improvement in terms of production amounts, concentration, and production rate per cell of the target organic acids, as well as simplification of the production process, and the like. Furthermore, techniques of increasing a non-amino organic acid-producing ability by DNA recombination have also been disclosed. For example, production of a non-amino organic acid by fermentation using a bacterium in which phosphoenolpyruvate carboxylase activity is enhanced (for example, Japanese Patent Laid-open No. 11-196887), and the like, have also been reported.

The entire genome sequence of a coryneform bacterium has been reported, and the functions of putative protein-coding sequences have been predicted (Appl. Microbiol. Biotechnol., 62 (2-3), 99-109 (2003)). The sucE1 gene is one of these putative protein-coding sequences, and although the gene is thought to code for a permease, the actual function has not been clarified. Finally, participation of the sucE1 gene in the succinic acid synthetic pathway was also not known. As for maleate dehydrogenase, although a method for producing succinic acid using a bacterium in which activity of this enzyme is enhanced has been reported (Japanese Patent Laid-open No. 2006-320208), the effect of enhancing the mdh gene along with the sucE1 gene has not been reported

SUMMARY OF THE INVENTION

An aspect of the present invention is to provide a method for producing an organic acid using a bacterium using a simplified production process.

It has been found that a bacterium which has been modified to enhance expression of the sucE1 and mdh genes can produce an organic acid from an organic raw material without the need for microaerobic induction.

It is an aspect of the present invention to provide a method for producing an organic acid comprising: A) allowing a substance to act on an organic raw material in a reaction mixture containing carbonate ions, bicarbonate ions, or carbon dioxide gas, wherein the substance is selected from the group consisting of: i) a bacterium which has an ability to produce an organic acid and has been modified to have enhanced expression of sucE1 and mdh genes, ii) a product obtained by processing the bacterium of i), and iii) combinations thereof, and B) collecting the organic acid.

It is a further aspect of the present invention to provide the aforementioned method, wherein expression of the sucE1 and mdh genes under aerobic conditions is increased by 1.5 times or more as compared to an unmodified strain.

It is a further aspect of the present invention to provide the aforementioned method, wherein the bacterium is selected from the group consisting of coryneform bacteria, *Bacillus* bacteria, and *Rhizobium* bacteria.

It is a further aspect of the present invention to provide the aforementioned method, wherein enhanced expression is obtained by a method selected from the group consisting of i) increasing the copy number of, ii) modifying an expression control sequence of the sucE1 gene and/or the mdh gene, iii) replacing a promoter of the sucE1 gene and/or the mdh gene with a stronger promoter, and iv) combinations thereof.

It is a further aspect of the present invention to provide the aforementioned method, wherein the stronger promoter is a constitutive expression promoter.

It is a further aspect of the present invention to provide the aforementioned method, wherein the stronger promoter is a promoter of a gene that encodes a protein selected from the group consisting of elongation factor Tu, cochaperonin GroES-chaperonin GroEL, thioredoxin reductase, phosphoglycerate mutase, peroxiredoxin, glycerol-3-phosphate dehydrogenase, 2,3-butanediol dehydrogenase, fructose bisphosphate aldolase, and superoxide dismutase.

It is a further aspect of the present invention to provide the aforementioned method, wherein the sucE1 gene is selected from the group consisting of: (a) a DNA comprising the nucleotide sequence of the numbers 571 to 2187 of SEQ ID NO: 3, and (b) a DNA which hybridizes with a nucleotide sequence complementary to the nucleotide sequence of the numbers 571 to 2187 of SEQ ID NO: 3 under stringent conditions, and the DNA improves the ability of the bacterium to produce succinic acid when expression of the DNA is enhanced in the bacterium.

It is a further aspect of the present invention to provide the aforementioned method, wherein the mdh gene is selected from the group consisting of: (a) a DNA comprising the nucleotide sequence of the numbers 301 to 1287 of SEQ ID NO: 13, and (b) a DNA which hybridizes with a nucleotide sequence complementary to the nucleotide sequence of the numbers 301 to 1287 of SEQ ID NO: 13 under stringent conditions, and codes for a protein having malate dehydrogenase activity.

It is a further aspect of the present invention to provide the aforementioned method, wherein the bacterium has been further modified so that lactate dehydrogenase activity is decreased to 10% or less of the activity as compared to lactate dehydrogenase activity in an unmodified strain.

It is a further aspect of the present invention to provide the aforementioned method, wherein the bacterium has been further modified so that pyruvate carboxylase activity is enhanced.

It is a further aspect of the present invention to provide the aforementioned method, wherein the organic acid is succinic acid.

It is a further aspect of the present invention to provide a method for producing a succinic acid-containing polymer comprising: A) producing succinic acid by the aforementioned method, and B) polymerizing the succinic acid.

It is a further aspect of the present invention to provide the aforementioned method, wherein the bacterium has been further modified so that succinate dehydrogenase activity is enhanced.

It is a further aspect of the present invention to provide the aforementioned method, wherein the organic acid is malic acid or fumaric acid.

It is a further aspect of the present invention to provide the aforementioned method, wherein the bacterium has been further modified so that succinate dehydrogenase activity is decreased to 10% or less as compared to succinate dehydrogenase activity in an unmodified strain.

BRIEF DESCRIPTION OF THE DRAWINGS

FIG. 1 shows construction of plasmid pBS4SΔldh56, which is used for ldh gene disruption.

DETAILED DESCRIPTION OF THE PREFERRED EMBODIMENTS

Hereinafter, embodiments of the present invention will be explained in detail.

Bacteria

The bacterium used in the method of the presently disclosed subject matter (also referred to as "the bacterium of the presently disclosed subject matter") can be a bacterium which has an ability to produce an organic acid and has been modified so that expression of both the sucE1 gene and the mdh gene are enhanced. This bacterium can be obtained by modifying a bacterium having an organic acid-producing ability as a parent strain so that expression of both the sucE1 gene and the mdh gene in the bacterium are simultaneously enhanced. When the parent strain is not able to produce an organic acid, the bacterium can be obtained by imparting this ability to the parent strain, and then modifying the strain so that expression of both the sucE1 gene and the mdh gene are enhanced. Furthermore, the bacterium can also be obtained by imparting an organic acid-producing ability to a strain which has previously been modified so that expression of both the sucE1 gene and the mdh gene are enhanced.

The organic acid can be a metabolic intermediate of the TCA cycle, and examples include succinic acid, malic acid, fumaric acid, citric acid, isocitric acid, cis-aconitic acid, and the like.

Parent strains that can be used to derive the bacteria of the presently disclosed subject matter are not particularly limited. However, aerobic bacteria and facultative anaerobic bacteria are examples, specifically, coryneform bacteria, *Bacillus* bacteria, *Rhizobium* bacteria, and *Escherichia* bacteria are also examples. Examples of coryneform bacteria include microorganisms belonging to the genus *Corynebacterium*, microorganisms belonging to the genus Brevibacterium, and microorganisms belonging to the genus *Arthrobacter*. Among these, those belonging to the genus *Corynebacterium* or Brevibacterium are examples. Microorganisms belonging to *Corynebacterium glutamicum*, Brevibacterium flavum, Brevibacterium ammoniagenes, or Brevibacterium lactofermentum are other examples.

Specific examples of the aforementioned parent strains of bacteria include Brevibacterium flavum MJ-233 (Agric. Biol. Chem., 54 (2), 443-447, 1990), MJ-233 AB-41, which is a mutant strain of MJ-233 (Japanese Patent Laid-open No. 2003-235592), *Corynebacterium glutamicum* (*Corynebacterium* sp., Brevibacterium flavum) AJ110655 (PERM ABP-10951), Brevibacterium ammoniagenes ATCC 6872, *Corynebacterium glutamicum* ATCC 31831, ATCC 13032, Brevibacterium lactofermentum ATCC 13869, and the like. Since Brevibacterium flavum can be currently classified into *Corynebacterium glutamicum* (Lielbl, W., Ehrmann, M., Ludwig, W. and Schleifer, K. H., International Journal of Systematic Bacteriology, 1991, vol. 41, pp. 255-260), the Brevibacterium flavum MJ-233 strain, MJ-233 AB-41 strain, and AJ110655 strain are considered to be identical to the *Corynebacterium glutamicum* MJ-233 strain, MJ-233 AB-41 strain, and AJ110655 strain, respectively.

The *Corynebacterium glutamicum* AJ110655 strain was deposited at the International Patent Organism Depositary, Agency of Industrial Science and Technology (Central 6, 1-1, Higashi 1-chome, Tsukuba-shi, Ibaraki-ken, Japan, 305-8566) on Feb. 15, 2008 and assigned a receipt number of FERM ABP-10951. The *Corynebacterium glutamicum* AJ110655 is an LDH gene-deficient strain constructed from the Brevibacterium flavum MJ-233 strain, and was deposited as the *Corynebacterium glutamicum* AJ110655 strain. Then, it was suggested that the species thereof was different from *Corynebacterium glutamicum* on the basis of nucleotide sequence analysis of 16S rRNA etc.

The parent strain which can be used to obtain the bacterium in accordance with the presently disclosed subject matter can be, besides wild-type strains, any strain, including mutant strains obtained by typical mutation treatments such as UV irradiation and NTG treatment, and recombinant strains induced by genetic procedures such as cell fusion and gene recombination techniques.

When the parent strain is not able to produce organic acids, this ability can be imparted by mutation or gene recombination. However, when the organic acid-producing ability is imparted by enhancing expression of the sucE1 gene and the mdh gene, it is not always necessary to impart the organic acid-producing ability by other means.

The "organic acid-producing ability" refers to an ability of the bacterium to cause accumulation of an organic acid in a reaction mixture containing carbonate ions, bicarbonate ions, or carbon dioxide to such an extent that the organic acid can be collected from the reaction mixture when the bacterium, or a product obtained by processing the bacterium, is allowed to act on a organic raw material in the reaction mixture.

The methods of imparting an organic acid-producing ability to a microorganism will be specifically explained below.

Succinic Acid-Producing Bacteria

Examples of the method for imparting or enhancing succinic acid-producing ability by breeding include, for example, modifying a bacterium so that expression of a gene coding for an enzyme involved in succinic acid biosynthesis is enhanced. Examples of enzymes involved in succinic acid biosynthesis include, for example, pyruvate carboxylase, fumarate reductase (Japanese Patent Laid-open No. 2005-095169), and the like. Bacteria in which the pyruvate carboxylase and fumarate reductase genes are amplified are described in Japanese Patent Laid-open based on International Patent Application (Kohyo) No. 2002-511250, Japanese Patent Laid-open Nos. 11-196888, 2005-95169, and the like.

Succinic acid-producing ability can also be imparted or enhanced by disrupting a gene coding for lactate dehydrogenase, which is an enzyme that is expressed under anaerobic conditions as described herein. Succinic acid-producing ability can also be imparted by treating a bacterium with ultraviolet rays or with a mutagen typically employed in mutation treatments such as N-methyl-N-nitro-N-nitrosoguanidine (NTG) or ethyl methanesulfonate (EMS), and selecting a strain which produces succinic acid. Examples of mutants having succinic acid-producing ability include the glutamic acid-auxotrophic strain disclosed in Japanese Patent Laid-open No. 2005-065641, and the like.

The bacterium can be obtained by modifying such a bacterium having succinic acid-producing ability as described above so that expression of the sucE1 gene and the mdh gene are enhanced. Either the modification for imparting succinic acid-producing ability or the modification for enhancing expression of the sucE1 gene and the mdh gene can be performed first.

sucE1 Gene

The protein encoded by the sucE1 gene (SucE, succinate exporter) is presumed to be a kind of permease, and is a protein which improves succinic acid-producing ability of a bacterium when expression of the gene is enhanced in the bacterium.

Examples of the sucE1 gene include the sucE1 gene derived from or native to Brevibacterium flavum MJ-233 (nucleotide numbers 571 to 2187 of SEQ ID NO: 3), the sucE1 gene derived from or native to *Corynebacterium glutamicum* ATCC 13032 (SEQ ID NO: 5), the sucE1 gene derived from or native to *Corynebacterium efficiens* YS314 (SEQ ID NO: 7), the sucE1 gene derived from or native to *Corynebacterium diphtheriae* gravis NCTC 13129 (SEQ ID NO: 11), and the like. The sucE1 gene derived from *C. glutamicum* ATCC 13032 is registered as NCg12130 in the genome sequence registered as GenBank Accession No. NC_003450 (amino acid sequence is registered as GenBank Accession No. NP_601414). The sucE1 gene derived from or native to *C. efficiens* YS314 is registered as CE2102 in the genome sequence registered as GenBank Accession No. NC_004369. The sucE1 gene derived from or native to *C. diphtheriae* gravis NCTC 13129 is registered as D1P0830 of GenBank Accession No. NC_002935.

A homologue gene of sucE1 derived from another microorganism can be used as the sucE1 gene so long as the homologous gene can improve succinic acid-producing ability of a bacterium when its expression is enhanced in the bacterium.

Homologues of the sucE1 gene can be searched for by using BLAST (//blast.genome.jp/), or the like, by referring to the sequence of the nucleotide numbers 571 to 2187 of SEQ ID NO: 3, and the like.

Since several sequences of the sucE1 gene have already been determined, the gene can be obtained by PCR using primers prepared on the basis of the nucleotide sequences. For example, a region including the structural sucE1 gene of *C. glutamicum* and a flanking region thereof including a control region of the gene can be obtained by PCR (polymerase chain reaction, see White, T. J. et al., Trends Genet., 5, 185 (1989)) using the primers shown in SEQ ID NOS: 1 and 2 and chromosomal DNA of a coryneform bacterium as the template. Homologues of sucE1 of other microorganisms can also be obtained in a similar manner.

Since the nucleotide sequence of the sucE1 gene is different depending on the species or strains of coryneform bacteria, the sucE1 gene is not limited to a gene having the sequence of the nucleotide numbers 571 to 2187 of SEQ ID NO: 3 or the sequence of SEQ ID NO: 5, 7 or 11, but it can also be a mutant or artificially modified gene that codes for a protein having a sequence of SEQ ID NO: 4, 6, 8 or 12 but which includes substitutions, deletions, insertions, additions, etc. of one or several amino acid residues at one or more positions. However, this mutated or artificially modified gene can still improve succinic acid-producing ability of the bacterium when expression of the gene is enhanced in the bacterium. Although the number meant by the term "several" in relation to the number of amino acid residues can differ depending on the position in the three-dimensional structure of the protein or the type of amino acid residue, it can be specifically 1 to 20, 1 to 10 in another example, or 1 to 5 in another example. The substitutions, deletions, insertions, additions, inversions or the like of amino acid residues described above can also include those caused by a naturally occurring mutation based on individual difference, difference in species of microorganisms from which the sucE1 gene is derived (mutant or variant), or the like.

The aforementioned substitution can be a conservative substitution that is a neutral substitution, that is, not resulting in a functional change. The conservative mutation is a mutation wherein substitution takes place mutually among Phe, Trp and Tyr, if the substitution site is an aromatic amino acid; among Leu, Ile and Val, if the substitution site is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having hydroxyl group. Specific examples of substitutions considered to be conservative substitutions can include: substitution of Ser or Thr for Ala; substitution of Gln, His or Lys for Arg; substitution of Glu, Gln, Lys, His or Asp for Asn; substitution of Asn, Glu or Gln for Asp; substitution of Ser or Ala for Cys; substitution of Asn, Glu, Lys, His, Asp or Arg for Gln; substitution of Gly, Asn, Gln, Lys or Asp for Glu; substitution of Pro for Gly; substitution of Asn, Lys, Gln, Arg or Tyr for His; substitution of Leu, Met, Val or Phe for Ile; substitution of Ile, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val.

Furthermore, as the sucE1 gene, a sequence encoding a protein having a homology not less than 80% in one example, not less than 90% in another example, not less than 95% in another example, or not less than 97% in another example, to the entire amino acid sequence of SEQ ID NOS: 4, 6, 8 or 12 and coding for a protein which improves succinic acid-producing ability of a bacterium when expression is enhanced in the bacterium can be used. Furthermore, the degree of degeneracy of a gene varies depending on the host into which the gene is introduced, and therefore codons can be replaced with those which are favorable for the chosen host of the sucE1. Moreover, the sucE1 gene can encode for a protein with an elongated or deleted N- or C-terminal sequence, so long as the gene improves the succinic acid-producing ability of a bacterium when expression is enhanced in the bacterium. The length of amino acid sequence to be elongated or deleted can be 50 or less, 20 or less in another example, 10 or less in another example, 5 or less in another example, in terms of number of amino acid residues. More specifically, the sucE1 gene can encode for a protein having the amino acid sequence of SEQ ID NO: 4, 6, 8 or 12 with elongation or deletion of 5 to 50 amino acid residues on the N-terminal or C-terminal side.

Genes which are homologous to the sucE1 gene as described above can be obtained by modifying the nucleotide sequence of nucleotide numbers 571 to 2187 of SEQ ID NO: 3, or the nucleotide sequence of SEQ ID NO: 5, 7 or 11 so that the protein encoded by the gene includes substitutions, deletions, insertions, or additions of amino acid residues at a specific site(s) by, for example, site-specific mutagenesis. Furthermore, homologous genes can also be obtained by conventionally known mutation treatments, such as those described below. Examples of mutation treatments include treating the nucleotide sequence of nucleotides 571 to 2187 of SEQ ID NO: 3, or the nucleotide sequence of SEQ ID NO: 5, 7 or 11, with hydroxylamine, or the like, in vitro, and treating a microorganism, for example, a coryneform bacterium, containing the gene with ultraviolet ray irradiation or a mutagen typically used for mutation such as N-methyl-N'-nitro-N-nitrosoguanidine (NTG) or ethyl methanesulfonate (EMS). Furthermore, a mutation can be artificially introduced into the sucE1 gene by gene recombination using error-prone PCR, DNA shuffling, or StEP-PCR to obtain a highly active sucE1 gene (Firth A. E., Patrick W. M., Bioinformatics., 21, 3314-3315, 2005 Jun. 2; Statistics of protein library construction).

Whether such homologous sucE1 genes code for a protein which improves succinic acid-producing ability when expression is enhanced can be confirmed by, for example, introducing these genes into a wild-type strain of a bacterium and determining whether the succinic acid-producing ability of the bacterium is improved or not.

Examples of the sucE1 gene also include a DNA that hybridizes with a sequence complementary to the sequence of nucleotides 571 to 2187 of SEQ ID NO: 3, the nucleotide sequence of SEQ ID NO: 5, 7 or 11, or a probe that can be prepared from the sequences under stringent conditions and codes for a protein which improves succinic acid-producing ability of a bacterium when expression is enhanced in the bacterium. The "stringent conditions" referred to herein are conditions under which a so-called specific hybrid is formed, and non-specific hybrid is not formed. Examples include, for example, conditions where DNAs showing high homology to each other, for example, DNAs showing a homology of, for example, not less than 80%, not less than 90% in another example, not less than 95% in another example, or not less than 97% in another example, hybridize with each other, and DNAs having homology lower than the above level do not hybridize with each other. Other examples include typical washing conditions in Southern hybridization, i.e., washing once, twice or three times, at salt concentrations and temperature of 1×SSC, 0.1% SDS at 60° C., or 0.1×SSC, 0.1% SDS at 60° C., or 0.1×SSC, 0.1% SDS at 68° C. in another example.

A partial sequence of the nucleotides 571 to 2187 of SEQ ID NO: 3 or a partial sequence of SEQ ID NO: 5, 7 or 11 can also be used as the probe. Such a probe can be prepared by PCR using oligonucleotides prepared on the basis of these nucleotide sequences as primers and a DNA fragment containing the sequence as the template. When a DNA fragment having a length of about 300 by is used as the probe, the washing conditions after hybridization under the aforementioned conditions can be exemplified by 2×SSC, 0.1% SDS at 50° C.

The expression "modified so that expression of sucE1 gene is enhanced" means that the number of SucE1 protein molecules per cell is increased, or that the activity per SucE1 protein molecule is increased, etc., as compared to an unmodified strain such as a parent strain or a wild-type strain. Examples of the wild-type coryneform bacterium which can be used for comparison include Corynebacterium glutamicum (Brevibacterium lactofermentum) ATCC 13869, ATCC 13032, and the like (the same shall apply to the other genes mentioned below).

Increase of expression level of the sucE1 gene can be confirmed by comparing the level of mRNA of sucE1 with that of an unmodified strain such as a parent strain or a wild-type strain. Examples of the method for confirming the expression level include Northern hybridization and RT-PCR (Molecular Cloning (Cold Spring Harbor Laboratory Press, Cold Spring Harbor (USA), 2001). The expression level of sucE1 can be any level so long as the level is increased as compared to that of an unmodified strain, and for example, it can be increased not less than 1.5 times, not less than 2 times in another example, or not less than 3 times in another example, as compared to that of an unmodified strain. The term "aerobic conditions" can mean that the dissolved oxygen concentration is not lower than 0.33 ppm and not higher than 7 ppm, or not lower than 1.5 ppm and not higher than 7 ppm in another example (Amino Acid Fermentation, Kunihiko Akashi et al.).

mdh Gene

The mdh gene is not particularly limited so long as it encodes for a protein having malate dehydrogenase activity, and examples include, for example, the gene derived from the Brevibacterium flavum MJ-233 strain having the nucleotide sequence shown in SEQ ID NO: 13. The phrase "malate dehydrogenase activity" can mean the activity for catalyzing the reaction of reducing oxaloacetic acid to malic acid, and the expression "malate dehydrogenase activity is enhanced" means that the malate dehydrogenase activity is enhanced as compared to that of a strain in which malate dehydrogenase is unmodified.

A homologue gene of mdh derived from another microorganism can be used as the mdh gene so long as the homologue gene codes for a protein having malate dehydrogenase activity. Homologues of the mdh gene can be searched for by using BLAST (http://blast.genome.jp/), or the like, by referring to the sequence of nucleotides 301 to 1384 of SEQ ID NO: 13.

Since several sequences of the mdh gene have already been determined as described above, homologous genes can be obtained by PCR using primers prepared on the basis of the known nucleotide sequences. For example, a region including the structural mdh gene of C. glutamicum and flanking regions, which include a control region of the gene, can be obtained by PCR using the primers shown in SEQ ID NOS: 15 and 16 and chromosomal DNA of the coryneform bacterium as the template. Homologues of mdh from other microorganisms can also be obtained in a similar manner.

The foregoing descriptions concerning mutants or artificially modified homologues of the sucE1 gene and protein are also applicable to the mdh gene. These descriptions are also applicable to the LDH gene and PC gene described later.

The expression "modified so that expression of mdh gene is enhanced" can mean that the bacterium is modified so that the activity of malate dehydrogenase encoded by the mdh gene is enhanced as compared to an mdh unmodified strain, such as a parent strain or a wild-type strain. This expression can also include when the number of malate dehydrogenase molecules per cell is increased, or when the activity per maleate dehydrogenase molecule is increased, etc. Examples of the wild-type coryneform bacterium which can be used for comparison include *Corynebacterium glutamicum* (Brevibacterium lactofermentum) ATCC 13869, ATCC 13032, and the like.

An increase in the expression of the mdh gene can be confirmed by comparing the level of the mdh mRNA with that of an unmodified strain as described above. An increase in the expression level of the mdh gene can also be confirmed by comparing the malate dehydrogenase activity with that of an unmodified strain.

The expression level of the mdh gene can be increased to any level so long as it is increased as compared to that of an unmodified strain under aerobic conditions, and for example, it can be increased not less than 1.5 times, and not less than 2 times in another example, as compared to an unmodified strain. The malate dehydrogenase activity can be measured by measuring the decrease of NADH as described later.

Enhancing Expression of the sucE1 and mdh Genes

Expression of the sucE1 gene and the mdh gene can be enhanced by increasing the copy numbers of these genes. For example, the copy numbers of the genes can be increased by ligating a fragment containing the genes to a vector which functions in the chosen bacterium, for example, a multi copy vector, to prepare a recombinant DNA, and transforming the bacterium as described above with the DNA. Alternatively, the copy numbers of the genes can be increased by transferring one copy or multiple copies of the genes to the bacterial chromosome. Transfer of the genes to the chromosome can be confirmed by Southern hybridization using a part of the genes as a probe.

When a plasmid vector is used, the sucE1 gene and the mdh gene can be carried on the same plasmid, or can be separately carried on different plasmids. Moreover, the order in which the sucE1 gene and the mdh gene are introduced into the bacterium is not limited, and they can be introduced simultaneously.

Expression of the sucE1 gene and the mdh gene can also be enhanced by modifying an expression control sequence of these genes. For example, a promoter sequence of the genes can be replaced with a stronger promoter, or the promoter sequence can be brought closer to a consensus sequence (WO00/18935).

Methods for modifying a microorganism so that expression of the sucE1 gene and the mdh gene are enhanced are specifically explained below. These methods can be performed as described in a manual such as Molecular Cloning (Cold Spring Harbor Laboratory Press, Cold Spring Harbor (USA), 2001).

First, a target gene can be cloned from the chromosome of a coryneform bacterium or the like. A chromosomal DNA can be prepared from a bacterium by, for example, the method of Saito and Miura (see H. Saito and K. Miura, Biochem. Biophys. Acta, 72, 619 (1963), Text for Bioengineering Experiments, Edited by the Society for Bioscience and Bioengineering, Japan, p 97-98, Baifukan Co., Ltd., 1992), or the like. Oligonucleotides for use in PCR can be synthesized on the basis of the aforementioned known information, for example, the synthetic oligonucleotides shown ins SEQ ID NOS: 1 and 2 can be used to amplify the sucE1 gene, and the synthetic oligonucleotides shown in SEQ ID NOS: 15 and 16 can be used to amplify the mdh gene.

A gene fragment which includes a gene amplified by PCR can itself be amplified by inserting the fragment into a vector having a replication origin that enables autonomous replication in the chosen bacterium, then transform the bacterium with the vector. In particular, when using a coryneform bacterium as the host, if a recombinant DNA is prepared by ligating the fragment to a vector DNA that is autonomously replicable in cells of *Escherichia coli* and a coryneform bacterium, and introduced into *Escherichia coli*, subsequent operations becomes easier. Examples of vectors that are autonomously replicable in cells of *Escherichia coli* include pUC19, pUC18, pHSG299, pHSG399, pHSG398, RSF1010, pBR322, pACYC184, pMW219, and the like.

Examples of plasmids that are autonomously replicable in coryneform bacteria include plasmids pCRY30 (described in Japanese Patent Laid-open No. 3-210184); plasmids pCRY21, pCRY2KE, pCRY2KX, pCRY31, pCRY3KE, and pCRY3KX (described in Japanese Patent Laid-open No. 2-72876 and U.S. Pat. No. 5,185,262); plasmids pCRY2 and pCRY3 (described in Japanese Patent Laid-open No. 1-191686); pAM330 (described in Japanese Patent Laid-open No. 58-67679); pHM1519 (described in Japanese Patent Laid-open No. 58-77895); pAJ655, pAJ611, and pAJ1844 (described in Japanese Patent Laid-open No. 58-192900); pCG1 (described in Japanese Patent Laid-open No. 57-134500); pCG2 (described in Japanese Patent Laid-open No. 58-35197); pCG4, pCG11 etc. (described in Japanese Patent Laid-open No. 57-183799); and pVK7 (described in Japanese Patent Laid-open No. 10-215883).

Furthermore, a vector obtained by excising a DNA fragment that enables a plasmid to autonomously replicate in coryneform bacteria from any of the above-listed vectors, and inserting the fragment into any of the aforementioned vectors for *Escherichia coli* can be used as a so-called shuttle vector, which is autonomously replicable both in *Escherichia coli* and coryneform bacteria.

To prepare a recombinant DNA by ligating the sucE1 gene and the mdh gene to a vector which functions in coryneform bacteria, the vector is digested with a restriction enzyme suitable for the ends of the genes. Such a restriction enzyme site can be introduced in advance into the synthetic oligonucleotide which is used to amplify the genes. Ligation is usually performed by using a ligase such as T4 DNA ligase.

In order to introduce a recombinant plasmid prepared as described above into a bacterium, any known transformation method reported to date can be employed. For example, recipient cells can be treated with calcium chloride so as to increase permeability for the DNA; this method has been reported for *Escherichia coli* K-12 (Mandel, M. and Higa, A., J. Mol. Biol., 53, 159 (1970)). Also, competent cells can be prepared from growing cells and DNA can be introduced into these cells; this method has been reported for *Bacillus subtilis* (Duncan, C. H., Wilson, G. A. and Young, F. E., Gene, 1, 153 (1977)). Another method is to make DNA recipient cells into protoplasts or spheroplasts which easily take up a recombinant DNA, and a recombinant DNA can be introduced into these cells; this method is known for *Bacillus subtilis*, actinomycetes, and yeasts (Chang, S, and Choen, S. N., Mol. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Acad. Sci. USA, 75, 1929 (1978)). In addition, bacteria can also be transformed by the electric pulse method (Japanese Patent Laid-open No. 2-207791) or by the conjugal transfer method (Biotechnology (NY). 1991 January; 9(1):84-7).

Copy numbers of the sucE1 and mdh genes can also be increased by integrating multiple copies of the genes into the chromosomal DNA of a bacterium, which can be accomplished by homologous recombination. This technique is performed by targeting a sequence which is present in multiple copies on the chromosomal DNA. Sequences present on the chromosomal DNA in multiple copies include repetitive DNA or inverted repeats present at the end of a transposable element. Alternatively, as disclosed in Japanese Patent Laid-open No. 2-109985, multiple copies of the genes can be introduced into a chromosomal DNA by incorporating them into a transposon and transferring it (Japanese Patent Laid-open Nos. 2-109985, 7-107976, Mol. Gen. Genet., 245, 397-405 (1994); Plasmid, 2000 November; 44(3): 285-91).

Another possible method is to insert the sucE1 gene and/or the mdh gene into a plasmid which has a replication origin that is not replicable or cannot replicate in the host, and which is able to cause conjugal transfer to the host, and introducing this plasmid into the host to amplify the gene on the chromosome. Examples of such a plasmid include pSUP301 (Simo et al., Bio/Technology 1, 784-791 (1983)), pK18mob or pK19mob (Schaefer et al., Gene 145, 69-73 (1994)), pGEM-T (Promega corporation, Madison, Wis., USA), pCR2.1-TOPO (Shuman (1994) Journal of Biological Chemistry 269: 32678-84; U.S. Pat. No. 5,487,993), pCR$^{(R)}$ Blunt (Invitrogen, Groningen, Netherlands; Bernard et al., Journal of Molecular Biology, 234: 534-541 (1993)), pEM1 (Schrumpf et al., 1991, Journal of Bacteriology 173: 4510-4516), pBGS8 (Spratt et al., 1986, Gene, 41:337-342), and the like. A plasmid vector which includes the sucE1 gene and/or the mdh gene is transferred into the bacterium by conjugation or transformation to transfer the genes onto the bacterial chromosome. The conjugation method is described by, for example, Schaefer et al. (Applied and Environmental Microbiology, 60, 756-759 (1994)). The transformation method is described by, for example, Theirbach et al. (Applied Microbiology and Biotechnology 29, 356-362 (1988)), Dunican and Shivinan (Bio/Technology 7, 1067-1070 (1989)), and Tauch et al. (NEMS Microbiological Letters 123, 343-347 (1994)). Expression of sucE1 and mdh can also be enhanced by replacing the native expression control sequences, such as promoters, of sucE1 and mdh on the chromosomal DNA or a plasmid with stronger promoters. For example, the lac promoter, trp promoter, trc promoter, PS2 promoter, and the like are known as strong promoters. Methods for evaluating the strength of promoters and examples of strong promoters are described in the paper of Goldstein et al. (Prokaryotic promoters in Biotechnology, Biotechnol. Annu. Rev., 1995, 1, 105-128), and the like. The strong promoter can be a constitutive expression promoter. The constitutive expression promoter can mean a promoter the expression of which is not changed by microaerobic induction. The term "microaerobic induction" can indicate a culture under microaerobic conditions, which imparts an activity of producing an organic acid under anaerobic conditions to cells which typically grow under aerobic conditions. The microaerobic conditions corresponds to 2 ppm or lower, 1 ppm or lower in another example, or 0.5 ppm or lower in another example, in terms of dissolved oxygen concentration with or without aeration. Moreover, the anaerobic condition is when the dissolved oxygen concentration is 0.5 ppm or lower when bubbling a gas other than oxygen, such as nitrogen or carbon dioxide.

The phrase "expression is not changed by microaerobic induction" means that the change in the ratio of the promoter activities observed before and after microaerobic induction is 3 times or smaller, 2 times or smaller in another example, or 1.5 times or smaller in another example. Specific examples of the constitutive expression promoter include promoters of genes coding for the elongation factor Tu (EF-Tu) (SEQ ID NO: 45), cochaperonin GroES-chaperonin GroEL (SEQ ID NO: 39), thioredoxin reductase (SEQ ID NO: 43), phosphoglycerate mutase (SEQ ID NO: 38), peroxiredoxin (SEQ ID NO: 40), glyceraldehyde 3-phosphate dehydrogenase (SEQ ID NO: 42), L-2,3-butanediol dehydrogenase (SEQ ID NO: 41), fructose bisphosphate aldolase (SEQ ID NO: 44), superoxide dismutase (SEQ ID NO: 37), and the like, but are not limited to these (WO2006/028063, European Patent No. 1697525).

The substitution of a stronger promoter can be combined with increasing the copy number of the sucE1 and mdh genes.

Expression of sucE1 and mdh can also be enhanced by modifying a factor involved in expression control such as an operator or a repressor, or ligating a strong terminator (Hamilton et al., Journal of Bacteriology 171: 4617-4622). Furthermore, as disclosed in WO00/18935, a promoter can be strengthened by making several nucleotide substitutions for nucleotides in the promoter region of a target gene so as to make the sequence closer to a consensus sequence. For example, the −35 region can be replaced with TTGACA or TTGCCA, and the −10 region can be replaced with TATAAT and TATAAC. In addition, it is known that the translation efficiency of mRNA is significantly affected by substitution of several nucleotides in the spacer sequence between the ribosome-binding site (RBS) and the translation initiation codon, in particular, the sequence immediately upstream of the initiation codon, and therefore, such a sequence can be modified.

Expression of a gene can also be enhanced by extending the survival time of the mRNA or by preventing degradation of an enzyme protein in cells. An expression control sequence, such as a promoter, which is upstream of the sucE1 or mdh gene can also be identified by using a promoter search vector or gene analysis software such as GENETYX. Expression of the sucE1 gene and the mdh gene can be enhanced by such promoter substitution or modification. An expression control sequence can be substituted by using, for example, a temperature-sensitive plasmid. Examples of temperature-sensitive plasmids for coryneform bacteria include p48K, pSFKT2 (for these, Japanese Patent Laid-open No. 2000-262288), pHSC4 (French Patent Laid-open No. 1992-2667875 and Japanese Patent Laid-open No. 5-7491), and the like. These plasmids are autonomously replicable at least at 25° C., but are not autonomously replicable at 37° C., in coryneform bacteria. Escherichia coli AJ12571 which harbors pHSC4 was deposited at the National Institute of Bioscience and Human-Technology, Agency of Industrial Science and Technology, Ministry of Trade and Industry (currently, International Patent Organism Depositary, National Institute of Advanced Industrial Science and Technology, Central 6, 1-1, Higashi 1-chome, Tsukuba-shi, Ibaraki-ken, Japan, 305-5466) on Oct. 11, 1990 and assigned an accession number of FERM P-11763, and this deposit was then converted to an international deposit under the provisions of Budapest Treaty on Aug. 26, 1991 and assigned an accession number of FERM BP-3524.

Modifying an expression control sequence can be combined with increasing copy numbers of the sucE1 gene and mdh gene.

Impartation of Other Properties

The bacterium in accordance with the presently disclosed subject matter can be modified so that the lactate dehydrogenase (LDH) activity is decreased, in addition enhancing expression of sucE and mdh. The expression "modified so that lactate dehydrogenase activity is decreased" can mean that the LDH activity is lower than that of a strain in which the LDH is unmodified, such as a parent strain or a wild-type strain. The lactate dehydrogenase activity per cell can be decreased to 10% or lower as compared to that of an unmodified strain. The "decrease" can include the complete deletion of the activity. Reduction of the LDH activity can be confirmed by measuring the LDH activity by a known method (Kanarek, L. and Hill, R. L., 1964, J. Biol. Chem., 239:4202). A coryneform bacterium in which the LDH activity is decreased and expression of the sucE1 and mdh genes are enhanced can be obtained by, for example, transforming a bacterium with a disrupted LDH gene with a recombinant vector containing the sucE1 and mdh genes, as described in the examples. However, either the modification for reducing the LDH activity or the modification for enhancing expression of the sucE1 and mdh genes can be performed first.

In order to decrease the activity of LDH, a mutation that decreases the intracellular activity of LDH can be introduced into the LDH gene on the chromosome by a usual mutagenesis method. For example, the gene coding for LDH on the chromosome can be deleted, or an expression control sequence such as a promoter and/or the Shine-Dalgarno (SD) sequence can be modified by gene recombination. Furthermore, a mutation which results in an amino acid substitution (missense mutation), a stop codon (nonsense mutation), or a frame shift mutation that adds or deletes one or two nucleotides into the LDH coding region on the chromosome can be introduced, or a part of the gene, or the entire gene, can be deleted (Journal of Biological Chemistry 272:8611-8617 (1997)). Furthermore, the LDH activity can also be decreased by mutating the LDH gene by deleting the coding region, and replacing the normal, or native LDH gene on the chromosome with the mutant LDH gene by homologous recombination or the like (Japanese Patent Laid-open No. 11-206385). Alternatively, a transposon or IS factor can be introduced into the genes, or the SacB gene can be used (Schafer, A. et al., Gene, 145 (1994) 69-73).

Gene substitution utilizing homologous recombination has already been established, and other methods include using a linear DNA, using a plasmid containing a temperature sensitive replication origin (U.S. Pat. No. 6,303,383, Japanese Patent Laid-open No. 5-7491), and the like.

In addition, in a process for disrupting a gene as described above, levansucrase can be used as a marker for gene recombination (Schafer, A. et al., Gene, 145 (1994) 69-73).

The bacterium can also be modified so that the pyruvate carboxylase (PC) activity is enhanced, in addition to the enhanced expression of the sucE1 and mdh genes (Japanese Patent Laid-open No. 11-196888). The expression "modified so that pyruvate carboxylase activity is enhanced" means that the PC activity is higher than that of an unmodified strain such as a wild-type strain or a parent strain. The PC activity can be measured by, for example, by measuring the decrease of NADH. A bacterium with enhanced expression of the sucE1, mdh and PC genes can be produced by overexpressing the sucE1, mdh and PC genes in the same manner as that described in Japanese Patent Laid-open No. 11-196888.

As the PC gene, a gene for which the nucleotide sequence is already determined, or a gene obtained by isolating a DNA fragment encoding a protein having the PC activity from a chromosome of a microorganism, animal, plant, or the like and determining the nucleotide sequence, can be used. After the nucleotide sequence is determined, a gene synthesized on the basis of that sequence can also be used.

As the PC gene, for example, a PC gene derived from, or native to, a coryneform bacterium such as *Corynebacterium glutamicum* (Peters-Wendisch, P. G. et al., 1998, Microbiology, vol. 144:915-927) (SEQ ID NO: 9) can be used. Furthermore, so long as the functions of the encoded PC, for example, being involved in carbon dioxide fixation, are not substantially degraded, the PC gene can be a mutant or modified gene.

The PC genes from bacteria other than *Corynebacterium glutamicum*, as well as from other microorganisms, animals, and plants can also be used. In particular, the reported sequences of PC genes derived from microorganisms, animals, and plants are described below (citations are indicated in brackets), and they can be obtained by hybridization or amplification by PCR of the ORF regions:

Human [Biochem. Biophys. Res. Comm., 202, 1009-1014, (1994)]
Mouse [Proc. Natl. Acad. Sci. USA., 90, 1766-1779, (1993)]
Rat [GENE, 165, 331-332, (1995)]
Yeast: *Saccharomyces cerevisiae* [Mol. Gen. Genet., 229, 307-315, (1991)], *Schizosaccharomyces pombe* [DDBJ Accession No.; D78170]
*Bacillus stearothermophilus* [GENE, 191, 47-50, (1997)]
*Rhizobium etli* [J. Bacteriol., 178, 5960-5970, (1996)]

The PC gene can be enhanced in the same manner as for enhancing expressions of the sucE1 and mdh genes as described above.

The bacterium can also be modified so that the acetyl-CoA hydrolase (ACH) activity is decreased, in addition to enhancing expression of sucE1 and mdh (WO2005/113744).

The "acetyl-CoA hydrolase (ACH) activity" can mean an activity for catalyzing the reaction to generate acetic acid from acetyl-CoA and water, and it is known that the amount of the by-product acetic acid can be decreased by reducing the ACH activity. The expression "modified so that activity of acetyl-CoA hydrolase is decreased" can mean that the activity of acetyl-CoA hydrolase is lower than the specific activity of an unmodified strain such as a parent strain or a wild-type strain. The ACH activity per cell can be decreased to 50% or less, 30% or less in another example, or 10% or less in another example, as compared to that of an unmodified strain. The activity of acetyl-CoA hydrolase can be determined by the method of Gergely, J., et al. (Gergely, J., Hele, P. & Ramkrishnan, C. V. (1952) J. Biol. Chem. 198 p323-334). The term "decreased" can mean the complete deletion of the activity. The coryneform bacterium with decreased ACH activity, and enhanced expression of the sucE1 and mdh genes, can be obtained by disrupting the ACH gene in the bacterium, and transforming the bacterium with a recombinant vector containing the sucE1 and mdh genes. However, either the modification for reducing the ACH activity or the modification for enhancing expressions of the sucE1 gene and the mdh gene can be performed first.

The bacterium can also be modified so that either or both of the activities of phosphotransacetylase (PTA) and acetate kinase (ACK) is/are decreased in addition to the enhanced expression of the sucE1 gene and the mdh gene. The phosphotransacetylase (PTA) activity can mean an activity for catalyzing the reaction to generate acetyl phosphate by transferring phosphate to acetyl-CoA (EC:2.3.1.8), and the acetate kinase (ACK) activity can mean an activity for catalyzing the reaction to generate acetic acid from acetyl phosphate and ADP (EC:2.7.2.1). The expression "phosphotransacetylase (PTA) activity is decreased" can mean that the PTA activity is lower than that of a strain in which the PTA is unmodified. Although it is sufficient that the PTA activity per cell is decreased so that it is lower than that of a strain in which the PTO is unmodified or a wild-type strain, it can be decreased to 50% or less, or 10% or less in another example, as compared to the activity of a strain in which the PTA is unmodified or a wild-type strain. The PTA activity can also be completely deleted. The decrease of the PTA activity can be confirmed by measuring the PTA activity by the method of Klotzsch et al. (Klotzsch H. R., Meth. Enzymol., 12, 381-386 (1969)). Furthermore, the expression "acetate kinase (ACK) activity is decreased" can mean that the ACK activity is lower than that of a strain in which the ACK unmodified. Although it is sufficient that the ACK activity per cell is decreased to be lower than that of a strain in which the ACK is unmodified or a wild-type strain, it can be decreased to 50% or less, 10% or less in another example, as compared to that of a strain in which the ACK is unmodified or a wild-type strain. The ACK activity can be completely deleted. The decrease in the ACK activity can be confirmed by measuring the ACK activity by the method of Irwin A. Rose (Rose, I. A., Meth. Enzymol., 1, 591-595 (1955)).

The coryneform bacterium in which either the activities of PTA and ACK are decreased, and expression of the sucE1 and mdh genes are enhanced can be obtained by, for example, producing a bacterium in which either the PTA or ACK gene is disrupted, and transforming the bacterium with a recombinant vector containing the sucE1 and mdh genes. However, either the modification for reducing either the PTA or ACK activity or the modification for enhancing expressions of the sucE1 gene and the mdh gene can be performed first.

The bacterium can be modified so that the pyruvate oxidase (POX) activity is decreased, in addition to increasing the expression of sucE1 and mdh (WO2005/113745).

The "pyruvate oxidase activity" can mean an activity for catalyzing the reaction to generate acetic acid from pyruvic acid and water. The expression "modified so that activity of pyruvate oxidase hydrolase is decreased" means that the POX activity is lower than that of a strain in which POX is unmodified. The POX activity per cell can be decreased to 50% or less, 30% or less in another example, 10% or less in another example, as compared to that of an unmodified strain. The term "decreased" can include the complete deletion of the activity. Examples of coryneform bacteria which can act as a control for comparison of the activity include, for example, Brevibacterium lactofermentum ATCC 13869 as a wild-type strain, and the Brevibacterium lactofermentum Δldh strain as an unmodified strain. The POX activity can be confirmed by measuring the activity by the method of Chang et al. (Chang Y. and Cronan J. E. JR, J. Bacteriol., 151, 1279-1289 (1982)). The coryneform bacterium in which the POX activity is decreased, and the expression of the sucE1 and mdh genes are enhanced, can be obtained by disrupting the POX gene in the bacterium, and transforming the bacterium with a recombinant vector containing the sucE1 and mdh genes. However, either the modification for decreasing the POX activity or the modification for enhancing expression of the sucE1 gene and the mdh gene can be performed first.

Furthermore, when the organic acid is succinic acid, the bacterium can be modified so that the activity of succinate dehydrogenase (SDH) is enhanced (Japanese Patent Laid-open No. 2005-095169), in addition to the enhanced expression of sucE1 and mdh. The expression "activity of succinate dehydrogenase is enhanced" means that the activity of SDH is higher than that of an unmodified strain such as a wild-type strain or a parent strain. The activity of SDH can be measured by measuring a decrease in NADH. A coryneform bacterium with enhanced expression of the sucE1, mdh, and SDH genes can be produced by overexpressing the sucE1, mdh, and SDH genes in the same manner as that described in Japanese Patent Laid-open No. 11-196888.

As the SDH gene, a previously reported SDH gene, or a gene obtained by isolating a DNA fragment coding for a protein having the SDH activity from a chromosome of a microorganism, animal or plant, and determining the nucleotide sequence, can be used. Moreover, after the nucleotide sequence is determined, a gene synthesized on the basis of the determined sequence can also be used. The sequences of the sdh operon of Corynebacterium glutamicum (GenBank accession Nos. NCg10359 (sdhC), NCg10360 (sdhA), NCg10361 (sdhB)), and the sdh operon of Brevibacterium flavum (Japanese Patent Laid-open No. 2005-095169, European Patent Laid-open No. 1672077) have been disclosed.

Furthermore, when the organic acid is malic acid or fumaric acid, the bacteria can be modified so that the activity of succinate dehydrogenase (SDH) is decreased, in addition to enhanced expression of sucE1 and mdh. It is known that, in Escherichia coli, if the activity of succinate reductase is insufficient, fumaric acid accumulation increases under anaerobic conditions (Journal of Industrial Microbiology & Biotechnology (2002) 28, 325-332). The expression "activity of succinate dehydrogenase is decreased" means that the activity of SDH is lower than that of an unmodified strain such as a wild-type strain or a parent strain. The succinate dehydrogenase activity per cell can be decreased to 10% or less of that of an unmodified strain. The activity of SDH can be measured by the aforementioned method.

The bacterium can have one of the "other properties" described above, or two or more of them.

Method for Producing an Organic Acid

The above-described bacterium which has an ability to produce an organic acid and has been modified to have enhanced expression of the sucE1 gene and mdh gene, or a product obtained by processing the bacterium, is allowed to act on an organic raw material in a reaction mixture containing carbonate ions, bicarbonate ions, or carbon dioxide gas to produce the organic acid, and the organic acid is collected.

In the one example of the method, by culturing the microorganism in a reaction mixture containing carbonate ions, bicarbonate ions, or carbon dioxide gas, and an organic raw material, proliferation of the microorganism and production of the organic acid are simultaneously attained. In this example, a medium can be the reaction mixture. Proliferation of the microorganism and production of the organic acid can be simultaneously attained, or there can be a period during the culture when proliferation of the microorganism mainly occurs, and a period during the culture when production of the organic acid mainly occurs.

In another example, by allowing cells to proliferate in a medium in the presence of carbonate ions, bicarbonate ions, or carbon dioxide gas, and an organic raw material, and thereby allowing the cells to act on the organic raw material in the medium, an organic acid is produced. In this example, a product obtained by processing the cells of the bacterium can also be used. Examples of a product obtained by processing the cells include, for example, immobilized cells, which can be obtained with the use of acrylamide, carragheenan, or the like, disrupted cells, centrifugation supernatant of the disrupted product, a fraction obtained by partial purification of the supernatant by ammonium sulfate treatment, or the like.

Although the bacteria can be obtained on a solid medium such as agar medium by slant culture, bacteria previously cultured in a liquid medium (seed culture) are also an example.

When an aerobic bacterium or a facultative anaerobic bacterium is used, the bacterial cells can be cultured under aerobic conditions first, and then used for the organic acid production reaction. Furthermore, although microaerobic induction is required for imparting an organic acid-producing activity to the cells when the cells are cultured under conventional aerobic conditions, it is not necessary. However, microaerobic induction can be performed. When microaerobic induction is performed, it can be performed for a period of 15 hours or shorter, 10 hours or shorter in another example, or 4 hours or shorter in another example, although the period can differ depending on the condition of the bacterium and degrees of microaerobic condition.

As the medium used for the culture, typical microorganism culture mediums can be used. For example, a typical medium obtained by adding natural nutrients such as meat extract, yeast extract, and peptone, to a composition that includes inorganic salts such as ammonium sulfate, potassium phosphate, and magnesium sulfate can be used.

In the aforementioned first example, the carbon source, which is added to the medium, also serves as the organic raw material for the production of the organic acid.

In the aforementioned second example, after the culture, the cells are collected by centrifugation, membrane separation, or the like, and used in the organic acid production reaction.

The organic raw material is not particularly limited so long as a carbon source, which the chosen microorganism can assimilate to produce an organic acid, is used. However, fermentable carbohydrates including carbohydrates such as galactose, lactose, glucose, fructose, glycerol, sucrose, saccharose, starch and cellulose, polyalcohols such as glycerin, mannitol, xylitol and ribitol, and the like are usually used. Among these, glucose, fructose and glycerol are examples.

Furthermore, a saccharified starch solution, molasses, or the like containing the fermentable carbohydrates can also be used. The fermentable carbohydrates can be used independently or in combination. Although the concentration of the aforementioned organic raw material is not particularly limited, it is more advantageous when the concentration is as high as possible within such a range that the culture of the microorganism and production of the organic acid are not inhibited. In the aforementioned first example, concentration of the organic raw material in the medium is generally in the range of 5 to 30% (w/v), or 10 to 20% (w/v) in another example. Furthermore, in the aforementioned second example, the concentration of the organic raw material in the reaction mixture is generally in the range of 5 to 30% (w/v), or 10 to 20% (w/v) in another example. Furthermore, additional organic raw material can be added as its concentration decreases with the progress of the reaction.

The aforementioned reaction mixture containing carbonate ions, bicarbonate ions, or carbon dioxide gas and the organic raw material is not particularly limited, and it can be, for example, a medium for culturing bacteria, or it can be a buffer such as phosphate buffer. The reaction mixture can be an aqueous solution containing a nitrogen source, inorganic salts, and the like. The nitrogen source is not particularly limited so long as it is a nitrogen source which the chosen microorganism can assimilate to produce an organic acid, and specific examples include various organic or inorganic nitrogen compounds such as ammonium salts, nitrates, urea, soybean hydrolysate, casein degradation products, peptone, yeast extract, meat extract, and corn steep liquor. As the inorganic salts, various phosphates, sulfates, and metallic salts such as those of magnesium, potassium, manganese, iron, and zinc can be used. If necessary, growth-promoting factors including vitamins such as biotin, pantothenic acid, inositol, and nicotinic acid, nucleotides, amino acids and the like can be added. In order to suppress foaming at the time of the reaction, an appropriate amount of commercially available antifoam can be added to the medium.

pH of the reaction mixture can be adjusted by adding sodium carbonate, sodium bicarbonate, potassium carbonate, potassium bicarbonate, magnesium carbonate, sodium hydroxide, calcium hydroxide, magnesium hydroxide, or the like. Since the pH for the reaction is usually 5 to 10, or 6 to 9.5 in another example, the pH of the reaction mixture is adjusted to be within the aforementioned range with an alkaline substance, carbonate, urea, or the like even during the reaction, if needed.

As the reaction mixture, water, buffer, medium or the like is used, but a medium is particular example. The medium can contain, for example, the aforementioned organic raw material, and carbonate ions, bicarbonate ions, or carbon dioxide gas, and the reaction can be performed under an anaerobic condition. The carbonate or bicarbonate ions can be supplied from magnesium carbonate, sodium carbonate, sodium bicarbonate, potassium carbonate, or potassium bicarbonate, which can also be used as a neutralizing agent. However, if necessary, carbonate or bicarbonate ions can also be supplied from carbonic acid or bicarbonic acid or salts thereof or carbon dioxide gas. Specific examples of the salts of carbonic acid or bicarbonic acid include, for example, magnesium carbonate, ammonium carbonate, sodium carbonate, potassium carbonate, ammonium bicarbonate, sodium bicarbonate, potassium bicarbonate, and the like. Carbonate ions or bicarbonate ions can be added at a concentration of 0.001 to 5 M, 0.1 to 3 M in another example, or 1 to 2 M in another example. When carbon dioxide gas is present, it can be present in the amount of 50 mg to 25 g, 100 mg to 15 g in another example, or 150 mg to 10 g in another example, per liter of the solution.

The optimal growth temperature of the bacterium is generally in the range of 25 to 35° C. The reaction temperature is generally in the range of 25 to 40° C., or in the range of 30 to 37° C. in another example. The amount of bacterial cells in the reaction mixture can be, although it is not particularly limited, 1 to 700 g/L, 10 to 500 g/L in an example, or 20 to 400 g/L in another example. The reaction time can be 1 to 168 hours, or 3 to 72 hours in another example. The reaction can be performed batch-wise or on a column The bacterial culture can be performed under aerobic conditions. Alternatively, the organic acid production reaction can be performed under aerobic conditions, microaerobic conditions, or anaerobic conditions. For the reaction under microaerobic conditions or anaerobic conditions, the reaction can be performed in a sealed reaction vessel without aeration, by supplying an inert gas such as nitrogen gas to the reaction mixture, by supplying an inert gas containing carbon dioxide gas to the reaction mixture, and the like.

The organic acid that accumulates in the reaction mixture (culture medium) can be separated and purified from the reaction mixture in a conventional manner. Specifically, solids such as bacterial cells can be removed by centrifugation, filtration, or the like, and then the resulting solution can be desalted with an ion exchange resin or the like. The organic acid can be separated and purified from the solution by crystallization or column chromatography.

Furthermore, when the target organic acid is succinic acid, after the succinic acid is produced, a polymerization reaction can be carried out by using the succinic acid to produce a polymer containing succinic acid. In recent years, with the increase of environmentally friendly industrial products, polymers prepared from raw materials of plant origin have been attracting attention. Succinic acid can be converted into polymers such as polyesters and polyamides and used (Japanese Patent Laid-open No. 4-189822). Specific examples of succinic acid-containing polymers include succinic acid polyesters obtainable by polymerizing a diol such as butanediol, ethylene glycol and succinic acid, succinic acid polyamides obtainable by polymerizing a diamine such as hexamethylenediamine and succinic acid, and the like. In addition, succinic acid and succinic acid-containing polymers, and compositions containing these can be used for food additives, pharmaceutical agents, cosmetics, and the like.

EXAMPLES

Hereinafter, the present invention will be explained more specifically with reference to the following non-limiting examples.

Example 1

Construction of a Strain in which the sucE1 and mdh Genes have Been Enhanced

<Construction of a Plasmid for Enhancement of sucE1>

An sucE1 gene fragment in which the native promoter is replaced with the thioredoxin reductase (TRR) promoter was obtained by crossover PCR using synthetic DNAs designed by referring to the nucleotide sequences around the TRR and the sucE1 gene of the genome sequence of *Corynebacterium glutamicum* ATCC 13032, which is publicly available (GenBank Database Accession No. NC_003450).

A sucE1 fragment containing the native promoter was amplified by PCR using the chromosome of Brevibacterium flavum MJ-233 as the template and the primers shown in SEQ ID NOS: 17 and 18. For PCR, Pyrobest DNA Polymerase (Takara Bio Inc.) was used, and the target PCR product was obtained by incubating at 94° for 3 minutes once, and then repeating a cycle of denaturation at 94° C. for 30 seconds, annealing at 60° C. for 30 seconds, and extension at 72° C. for 1 minute 30 times. The PCR product was treated with Sse8387I, and the product was inserted into pVK9 at the Sse8387I site to construct a plasmid pVK9sucE1 carrying sucE1 gene containing the native promoter. By treating this plasmid with XbaI and BstXI, a part of the ORF of the sucE1 gene containing the native promoter can be excised.

Furthermore, a fragment (A) containing the N-terminal sequence of the sucE1 gene was amplified by PCR using the chromosome of Brevibacterium flavum MJ-233 as the template and the primers shown in SEQ ID NOS: 19 and 20. Separately, a thioredoxin reductase (TRR) promoter fragment (B) was amplified by PCR using the chromosome of Brevibacterium flavum MJ-233 as the template and the primers shown in SEQ ID NOS: 21 and 22. In the PCR of both cases, PrimeSTAR HS DNA Polymerase (TaKaRa) was used, incubation was performed once at 98° for 2 minutes, and then a cycle of denaturation at 98° C. for 10 seconds, annealing at 55° C. for 5 seconds, and extension at 72° C. for 20 seconds was repeated 30 times to obtain the target PCR products (A) and (B). The sequences of SEQ ID NOS: 19 and 22 are complementary to each other.

Then, a fragment containing the N-terminal sequence of sucE1 in which the native promoter is replaced with the TRR promoter was constructed by crossover PCR using the fragments (A) and (B) as the templates and the primers shown in SEQ ID NOS: 20 and 21. In the PCR, PrimeSTAR HS DNA Polymerase (Takara Bio Inc.) was used, incubation was performed once at 98° for 2 minutes, and then a cycle of denaturation at 98° C. for 10 seconds, annealing at 55° C. for 5 seconds, and extension at 72° C. for 40 seconds was repeated 30 times to obtain the target PCR product. The PCR product was purified in a conventional manner, treated with XbaI and BstXI, and then inserted into pVK9sucE1 at the XbaI and BstXI sites to construct a sucE1 amplification plasmid, pVK9:PTRR-sucE1, in which the native promoter was replaced with the TRR promoter.

pVK9 is a shuttle vector obtained by blunt-ending the AvaII site of pHSG299 (Takara Bio), and inserting a fragment, obtained by excising a region autonomously replicable in coryneform bacteria contained in pHK4 (Japanese Patent Laid-open No. 5-007491) with BamHI and KpnI and blunt-ending the excised region, into the above pHSG299 at the blunt-ended AvaII site.

<Construction of a Plasmid for Enhancement of mdh>

An mdh gene fragment in which the native promoter is replaced with the elongation factor Tu (ET-Tu) promoter was obtained by crossover PCR using synthetic DNAs designed by referring to nucleotide sequences around EF-Tu and the mdh gene of the genome sequence of *Corynebacterium glutamicum* ATCC 13032, which is publicly available (GenBank Database Accession No. NC_003450), as primers.

Specifically, an mdh fragment containing the native promoter was amplified by PCR using the chromosome of Brevibacterium flavum MJ-233 as the template and the primers shown in SEQ ID NOS: 23 and 24. In the PCR, Pyrobest DNA Polymerase (Takara Bio Inc.) was used, incubation was performed once at 94° for 2 minutes, and then a cycle of denaturation at 94° C. for 30 seconds, annealing at 57° C. for 30 seconds, and extension at 72° C. for 1 minute and 30 seconds was repeated 30 times to obtain the target PCR product. The PCR product was treated with XbaI and Sse8387I, and then inserted into pVK9 at the XbaI and Sse8387I sites to construct a plasmid pVK9mdh carrying mdh containing the native promoter. A part of the ORF of mdh containing the native promoter can be excised from this plasmid by treating the plasmid with BamHI and MluI.

Furthermore, a fragment (C) containing an N-terminal sequence of mdh was amplified by PCR using the chromosome of Brevibacterium flavum MJ-233 as the template and the primers shown in SEQ ID NOS: 25 and 26. Separately, an EF-Tu promoter fragment (D) was amplified by PCR using the chromosome of Brevibacterium flavum MJ-233 as the template and the primers shown in SEQ ID NOS: 27 and 28. In both PCR, PrimeSTAR HS DNA Polymerase (Takara Bio Inc.) was used, incubation was performed once at 98° for 2 minutes, and then a cycle of denaturation at 98° C. for 10 seconds, annealing at 55° C. for 5 seconds, and extension at 72° C. for 20 seconds was repeated 30 times to obtain the target PCR products (C) and (D). The sequences of SEQ ID NOS: 25 and 28 are complementary to each other.

Then, a fragment containing the N-terminal sequence of mdh in which the native promoter is replaced with the EF-Tu promoter was constructed by crossover PCR using the fragments (C) and (D) as the templates and the primers shown in SEQ ID NOS: 27 and 26. In the PCR, PrimeSTAR HS DNA Polymerase (Takara Bio Inc.) was used, incubation was performed once at 98° for 2 minutes, and then a cycle of denaturation at 98° C. for 10 seconds, annealing at 55° C. for 5 seconds, and extension at 72° C. for 40 seconds was repeated 30 times to obtain the target PCR product. The PCR product was purified in a conventional manner, treated with BamHI and MluI, and then inserted into pVK9mdh at the BamHI and MluI sites to construct a mdh amplification plasmid, pVK9:PEFTu-mdh, in which the native promoter was replaced with the EF-Tu promoter.

<Construction of a Plasmid for Enhancement of sucE1 and mdh>

A plasmid carrying both the sucE1 and mdh genes was constructed as follows.

First, an mdh gene fragment in which the native promoter was replaced with the ET-Tu promoter was obtained by crossover PCR using synthetic DNAs designed by referring to nucleotide sequences around EF-Tu and the mdh gene of the genome sequence of *Corynebacterium glutamicum* ATCC 13032, which is publicly available (GenBank Database Accession No. NC_003450), as primers.

A fragment (G) containing the ORF of mdh was amplified by PCR using the chromosome of Brevibacterium flavum MJ-233 as the template and the primers shown in SEQ ID NOS: 25 and 29. In the PCR, PrimeSTAR HS DNA Polymerase (Takara Bio Inc.) was used, incubation was performed once at 98° for 2 minutes, and then a cycle of denaturation at 98° C. for 10 seconds, annealing at 55° C. for 5 seconds, and extension at 72° C. for 1 minute was repeated 30 times to obtain the target PCR product (G). Separately, an EF-Tu promoter fragment (H) was amplified by PCR using the chromosome of Brevibacterium flavum MJ-233 as the template and the primers shown in SEQ ID NOS: 30 and 28. In the PCR, PrimeSTAR HS DNA Polymerase (Takara Bio Inc.) was used, incubation was performed once at 98° for 2 minutes, and then a cycle of denaturation at 98° C. for 10 seconds, annealing at 55° C. for 5 seconds, and extension at 72° C. for 20 seconds was repeated 30 times to obtain the target PCR product (H). The sequences of SEQ ID NOS: 25 and 27 are complementary to each other.

Then, a fragment containing ORF of mdh in which the native promoter was replaced with the EF-Tu promoter was constructed by crossover PCR using the fragments (G) and (H) as the templates and the primer shown in SEQ ID NOS: 29 and 30. In the PCR, PrimeSTAR HS DNA Polymerase (Takara Bio Inc.) was used, incubation was performed once at 98° for 2 minutes, and then a cycle of denaturation at 98° C. for 10 seconds, annealing at 55° C. for 5 seconds, and extension at 72° C. for 1 minute and 20 seconds was repeated 30 times to obtain the target PCR product. The PCR product was purified in a conventional manner, treated with SpeI and Sse8387I, and then inserted into pVK9:PTRR-sucE1 at the SpeI and Sse8387I sites to construct a plasmid carrying both sucE1 and mdh, pVK9:PTRR-sucE1+PEFTu-mdh.

A plasmid carrying both sucE1 and mdh can be constructed in the same manner by using chromosomal DNA of a strain other than the MJ-233 strain such as the *Corynebacterium glutamicum* AJ110655 strain as the template.

<Construction of ldh Gene-Disrupted Strain>

(A) Cloning of a Fragment to Disrupt the ldh Gene

A gene fragment of the ldh gene deficient in the ORF was obtained by crossover PCR using synthetic DNAs designed by referring to the nucleotide sequence around NCg12817 of the genome sequence of *Corynebacterium glutamicum* ATCC 13032, which is publicly available (GenBank Database Accession No. NC_003450), as primers. PCR was performed using the chromosomal DNA of Brevibacterium lactofermentum 2256 strain (ATCC 13869) as the template and the synthetic DNAs of SEQ ID NOS: 31 and 32 as primers to obtain an amplification product of an N-terminal sequence of the ldh gene. Separately, to obtain an amplification product of a C-terminal sequence of the ldh gene, PCR was performed by using the chromosomal DNA of Brevibacterium lactofermentum 2256 strain as the template and the synthetic DNAs of SEQ ID NOS: 33 and 34 as primers. In the PCR, Pyrobest DNA Polymerase (Takara Bio Inc.) was used, and each target PCR product was obtained by performing incubation at 94° for 3 minutes once, and then repeating a cycle of denaturation at 94° C. for 30 seconds, annealing at 60° C. for 30 seconds, and extension at 72° C. for 1 minute 30 times. The sequences of SEQ ID NOS: 32 and 33 are complementary to each other. Then, to obtain an ldh gene fragment in which the internal sequence is deleted, the above gene products of the N-terminal and C-terminal regions of ldh were mixed in approximately equimolar amounts, and PCR was performed using the mixture as the template and synthetic DNAs of SEQ ID NOS: 35 and 36 as primers to obtain an amplification product in which of ORF of ldh is deleted. In the PCR, Pyrobest DNA Polymerase (Takara Bio Inc.) was used, and the target PCR product was obtained by performing incubation at 94° for 3 minutes once, and then repeating a cycle of denaturation at 94° C. for 30 seconds, annealing at 58° C. for 30 seconds, and extension at 72° C. for 2 minute 30 times. The PCR product was purified in a conventional manner, then digested with BamHI, and inserted into a vector pBS4S for gene disruption (WO2007/046389) at the BamHI site to obtain a plasmid for ldh gene disruption, pBS4SΔldh56. The construction of this plasmid is shown in FIG. 1.

(B) Production of ldh-Disrupted Strain

The pBS4SΔldh56 obtained in (A) described above does not contain a region that enables autonomous replication in a cell of coryneform bacteria. Therefore, when a coryneform bacterium is transformed with this plasmid, the strain in which the plasmid is integrated into the chromosome by homologous recombination appears as a transformant, although it occurs at an extremely low frequency. The Brevibacterium lactofermentum 2256 strain was transformed with a high concentration of the plasmid pBS4SΔldh56 by the electric pulse method, and the transformed cells were applied onto CM-Dex agar medium (5 g/L of glucose, 10 g/L of polypeptone, 10 g/L of yeast extract, 1 g/L of $KH_2PO_4$, 0.4 g/L of $MgSO_4.7H_2O$, 0.01 g/L of $FeSO_4.7H_2O$, 0.01 g/L of $MnSO_4.7H_2O$, 3 g/L of urea, 1.2 g/L of soybean hydrolysate, pH 7.5 (KOH) containing 1.5% of agar) containing 50 μg/ml of kanamycin, and cultured at 31.5° C. for about 24 hours. The plasmid used for the transformation of MJ-233 was obtained by transforming a dam methylase-deficient strain, *Escherichia coli* SCS110 strain (Stratagene), with pBS4SAΔldh56, and extracting the plasmid from this strain. In the strains of colonies that appeared, the kanamycin resistance gene and the sacB gene derived from the plasmid were inserted into the genome as a result of homologous recombination between the ldh gene fragment on the plasmid and the ldh gene on the genome of Brevibacterium flavum MJ-233 strain.

Then, these single recombinants were cultured overnight at 31.5° C. in the CM-Dex liquid medium not containing kanamycin, then appropriately diluted, applied to 10% sucrose-containing Dex-S10 medium (100 g/L of sucrose, 10 g/L of polypeptone, 10 g/L of yeast extract, 1 g/L of $KH_2PO_4$, 0.4 g/L of $MgSO_4.7H_2O$, 0.01 g/L of $FeSO_4.7H_2O$, 0.01 g/L of $MnSO_4.4H_2O$, 3 g/L of urea, 1.2 g/L of soybean hydrolysate, 10 μg/L of biotin, pH 7.5 (KOH) containing 1.5% of agar) not containing kanamycin, and cultured at 31.5° C. for about 24 hours to obtain clones which are resistant to sucrose. These strains no longer expressed the normal sacB gene, and included strains in which pBS4SAΔldh56 was eliminated by the second homologous recombination. Furthermore, the strains which had undergone the second homologous recombination included a strain in which the ldh gene was replaced with the deletion-type gene derived from pBS4SΔldh56 and a strain in which the ldh gene had reverted back to the wild-type gene. Whether the ldh gene is the mutant or the wild-type can be easily confirmed by extracting chromosomal DNA from cells obtained by culture on the Dex-S10 agar medium, and detecting the ldh gene in the chromosomal DNA by PCR. Among the double recombinant strains, after amplification using the primers for PCR amplification of the ldh gene (SEQ ID NOS: 31 and 34), a strain which provided a PCR product smaller than the PCR product obtained by using the chromosomal DNA of the MJ-233 strain was determined to be an ldh-deficient strain, and was used in the following experiments. The ldh-deficient strain was designated as AJ110655.

<Construction of sucE1-Amplified Strain, mdh-Amplified Strain, and sucE1+mdh-Amplified Strain>

The *Corynebacterium glutamicum* AJ110655 strain was transformed with pVK9:PTRR-sucE1, pVK9:PEFTu-mdh, pVK9:PTRR-sucE1+PEFTu-mdh obtained above, and pVK9, by the electric pulse method, applied to the CM-Dex agar medium containing 25 µg/ml of kanamycin, and cultured at 31.5° C. for about 24 hours to obtain strains into which each of the plasmids were introduced. The colonies that appeared were purified, and plasmids were extracted in a conventional manner to confirm introduction of each target plasmid.

Example 2

Succinic Acid Production with the sucE1- and mdh-Amplified Strain

Using strains obtained by introducing each of pVK9, the plasmid for enhanced sucE1 gene alone (pVK9:PTRR-sucE1), the plasmid for enhanced mdh gene alone (pVK9:PEFTu-mdh), and the plasmid for enhanced sucE1 and mdh genes together (pVK9:PTRR-sucE1+PEFTu-mdh), into the *Corynebacterium glutamicum* AJ110655 strain, and the culture for succinic acid production was performed as follows. Cells of each strain obtained by culturing the strain on a CM-Dex plate medium were inoculated into 20 ml of a seed medium (25 g/L of glucose, 1.4 g/L of $(NH_4)_2SO_4$, 0.5 g/L of $KH_2PO_4$, 0.5 g/L of $K_2HPO_4$, 0.5 g/L of $MgSO_4.7H_2O$, 4 g/L of urea, 0.02 g/L of $FeSO_4.7H_2O$, 0.02 g/L of $MnSO_4.7H_2O$, 200 µg/L of biotin, 200 µg/L of VB1.HCl, 1 g/L of yeast extract, 1 g/L of casamino acid, 25 mg/L of kanamycin), and cultured at 31.5° C. in a Sakaguchi flask under an aerobic conditions with shaking for about 5 hours (aerobic culture) or 16 hours (microaerobic induction culture).

Then, 700 µl of the seed medium was isolated, and immediately mixed with 700 µl of a main medium (200 g/L of glucose, 30 g/L of Na sulfite, filtrated and mixed with 143 g/L as the final concentration of magnesium carbonate subjected to hot air sterilization) contained in a micro tube (Eppendorf tube), and the culture was performed at 31.5° C. with shaking. The culture was terminated after 48 hours, and the amount of succinic acid which was produced was analyzed by liquid chromatography. Two of Shim-pack SCR-102H (Shimadzu) connected in series were used as the column, and a sample was eluted at 40° C. with 5 mM p-toluenesulfonic acid. The eluate was neutralized with 20 mM Bis-Tris aqueous solution containing 5 mM p-toluenesulfonic acid and 100 µM EDTA, and succinic acid was quantified by measuring electric conductivity with CDD-10AD (Shimadzu).

When the microaerobically cultured cells obtained when microaerobic induction was performed, i.e., obtained with the seed culture of 16 hours, were used, the amount of succinic acid which accumulated per cell was equivalent in all the transformants. Alternatively, when the aerobically cultured cells obtained when the microaerobic induction was not performed, i.e., obtained with the seed culture of 5 hours, were used, only the pVK9:PTRR-sucE1+PEFTu-mdh-introduced strain produced an amount of succinic acid higher than those obtained with the cells obtained with microaerobic induction, whereas the pVK9-introduced strain, pVK9:PTRR-sucE1-introduced strain, and pVK9:PEFTu-mdh-introduced strain did not produce succinic acid during the main culture. The results are shown in Table 1.

From these results, it was demonstrated that production of succinic acid can be imparted in a strain in which expression of both the sucE1 and mdh genes are enhanced, when the strain is cultured under aerobic conditions, and not under microaerobic conditions, and is effective for fermentative production of succinic acid.

TABLE 1

| | Succinic acid accumulation amount (g/L/O.D.620 = 1) | |
|---|---|---|
| Strain | Aerobically cultured cells | Microaerobically cultured cells |
| AJ110655/pVK9 | 0.6 | 1.6 |
| AJ110655/pVK9: PTRR-sucE1 | 0.7 | 1.8 |
| AJ110655/pVK9: PEFTu-mdh | 0.5 | 1.9 |
| AJ110655/pVK9: PTRR-sucE1 + PEFTu-mdh | 2.0 | 1.7 |

Explanation of Sequence Listing

SEQ ID NO: 1: Primer for sucE1 gene amplification
SEQ ID NO: 2: Primer for sucE1 gene amplification
SEQ ID NO: 3: Nucleotide sequence of sucE1 gene of B. flavum MJ-233
SEQ ID NO: 4: Amino acid sequence encoded by the sucE1 gene mentioned above
SEQ ID NO: 5: sucE1 gene of *C. glutamicum* ATCC 13032
SEQ ID NO: 6: Amino acid sequence encoded by the sucE1 gene mentioned above
SEQ ID NO: 7: Nucleotide sequence of sucE1 gene derived from *C. efficiens* YS314
SEQ ID NO: 8: Amino acid sequence encoded by the sucE1 gene mentioned above
SEQ ID NO: 9: Nucleotide sequence of PC gene of *C. glutamicum*
SEQ ID NO: 10: Amino acid sequence encoded by the PC gene mentioned above
SEQ ID NO: 11: Nucleotide sequence of sucE1 gene of *C. diphtheriae* gravis NCTC 13129
SEQ ID NO: 12: Amino acid sequence encoded by the sucE1 gene mentioned above
SEQ ID NO: 13: Nucleotide sequence of mdh gene of B. flavum MJ-233
SEQ ID NO: 14: Amino acid sequence encoded by the mdh gene mentioned above
SEQ ID NO: 15: Primer for mdh gene amplification
SEQ ID NO: 16: Primer for mdh gene amplification
SEQ ID NO: 17: Primer for amplification of sucE1 fragment containing native promoter
SEQ ID NO: 18: Primer for amplification of sucE1 fragment containing native promoter
SEQ ID NO: 19: Primer for amplification of fragment (A) containing N-terminal sequence of sucE1
SEQ ID NO: 20: Primer for amplification of fragment (A) containing the N terminal sequence of sucE1
SEQ ID NO: 21: Primer for amplification of TRR promoter fragment (B)
SEQ ID NO: 22: Primer for amplification of TRR promoter fragment (B)
SEQ ID NO: 23: Primer for amplification of mdh fragment containing native promoter
SEQ ID NO: 24: Primer for amplification of mdh fragment containing native promoter
SEQ ID NO: 25: Primer for amplification of fragment (C) or (G) containing N-terminal sequence of mdh
SEQ ID NO: 26: Primer for amplification of fragment (C) containing N-terminal sequence of mdh
SEQ ID NO: 27: Primer for amplification of EF-Tu promoter fragment (D)

SEQ ID NO: 28: Primer for amplification of EF-Tu promoter fragment (D) or (H)

SEQ ID NO: 29: Primer for amplification of fragment (G) containing mdh gene

SEQ ID NO: 30: Primer for amplification of EF-Tu promoter fragment (H)

SEQ ID NO: 31: Primer for production of fragment for ldh gene disruption (N-terminal sequence)

SEQ ID NO: 32: Primer for Production of Fragment for Ldh Gene Disruption (N-terminal sequence)

SEQ ID NO: 33: Primer for production of fragment for ldh gene disruption (C-terminal sequence)

SEQ ID NO: 34: Primer for production of fragment for ldh gene disruption (C-terminal sequence)

SEQ ID NO: 35: Primer for production of fragment for ldh gene disruption

SEQ ID NO: 36: Primer for production of fragment for ldh gene disruption

SEQ ID NO: 37: Nucleotide sequence of superoxide dismutase gene promoter of *C. glutamicum* ATCC 13032

SEQ ID NO: 38: Nucleotide sequence of phosphoglycerate mutase gene promoter of *C. glutamicum* ATCC 13032

SEQ ID NO: 39: Nucleotide sequence of GroES-GroEL operon promoter of *C. glutamicum* ATCC 13032

SEQ ID NO: 40: Nucleotide sequence of peroxiredoxin gene promoter of *C. glutamicum* ATCC 13032

SEQ ID NO: 41: Nucleotide sequence of butanediol dehydrogenase gene promoter of *C. glutamicum* ATCC 13032

SEQ ID NO: 42: Nucleotide sequence of glyceraldehyde 3-phosphate dehydrogenase gene promoter of *C. glutamicum* ATCC 13032

SEQ ID NO: 43: Nucleotide sequence of thioredoxin reductase gene promoter of *C. glutamicum* ATCC 13032

SEQ ID NO: 44: Nucleotide sequence of fructose bisphosphate aldolase gene promoter of *C. glutamicum* ATCC 13032

SEQ ID NO: 45: Nucleotide sequence of EF-Tu gene promoter of B. flavum MJ-233

Industrial Applicability

According to the method of the present invention, an organic acid can be quickly and highly efficiently produced from an organic raw material by using aerobically cultured cells without need of microaerobic induction. The obtained organic acid can be used for food additives, pharmaceuticals, cosmetics, and the like. Moreover, organic acid-containing polymers can also be produced by performing a polymerization reaction using the obtained organic acid as a raw material.

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for producing an organic acid comprising:

A) allowing a substance to act on an organic raw material in a reaction mixture containing carbonate ions, bicarbonate ions, or carbon dioxide gas, wherein the substance is selected from the group consisting of:
   i) a bacterium which has an ability to produce an organic acid and has been modified to have enhanced expression of the sucE1 and mdh genes,
   ii) a product obtained by processing the bacterium of i), and
   iii) combinations thereof, and B) collecting the organic acid, wherein the sucE1 gene is selected from the group consisting of:
   (a) a DNA comprising the nucleotide sequence of numbers 571 to 2187 of SEQ ID NO: 3, or the nucleotide sequence of SEQ ID NOs: 5, 7 or 11,
   (b) a DNA which hybridizes with a nucleotide sequence complementary to the nucleotide sequence of the numbers 571 to 2187 of SEQ IS NO: 3, or the nucleotide sequence of SEQ ID NOs: 5, 7 or 11, under stringent conditions comprising washing at 0.1x SSC, 0.1% SDS at 68° C., and wherein the DNA improves the ability of the bacterium to produce succinic acid when expression of the DNA is enhanced in the bacterium,
   (c) a DNA which encodes a protein having the amino acid sequence of SEQ ID NOs: 4, 6, 8, or 12, and
   (d) a DNA which encodes a protein having a homology of not less than 95% to the amino acid sequence of SEQ ID NOs: 4, 6, 8, or 12, and wherein said protein improves the ability of the bacterium to produce succinic acid when expression of the DNA is enhanced in the bacterium, wherein the mdh gene is selected from the group consisting of:
   (A) a DNA comprising the nucleotide sequence of the numbers 301 to 1287 of SEQ ID NO: 13,
   (B) a DNA which hybridizes with a nucleotide sequence complementary to the nucleotide sequence of the numbers 301 to 1287 of SEQ ID NO: 13 under stringent conditions comprising washing at 0.1x SSC, 0.1% SDS at 68° C., and codes for a protein having malate dehydrogenase activity,
   (C) a DNA encoding a protein having the amino acid sequence of SEQ ID NO: 14, and
   (D) a DNA encoding a protein having a homology not less than 95% to the entire amino acid sequence of SEQ ID NO: 14, and wherein said protein has malate dehydrogenase activity, and wherein enhanced expression is obtained by a method selected from the group consisting of
   i) increasing the copy number of the sucE1 gene and/or the mdh gene,
   ii) modifying an expression control sequence of the sucE1 gene and/or the mdh gene,
   iii) replacing a promoter of the sucE1 gene and/or the mdh gene with a stronger promoter, and
   iv) combinations thereof.

2. The method according claim 1, wherein expression of the sucE1 and mdh genes under aerobic conditions is enhanced by 1.5 times or more as compared to an unmodified bacterium.

3. The method according to claim 1, wherein the bacterium is selected from the group consisting of coryneform bacteria, *Bacillus* bacteria, and *Rhizobium* bacteria.

4. The method according to claim 1, wherein enhanced expression of the sucE1 gene and/or mdh gene is obtained by replacing the promoter of the sucE1 gene and/or mdh gene with a stronger promoter that is a constitutive expression promoter.

5. The method according to claim 4, wherein the stronger promoter is a promoter of a gene that encodes a protein selected from the group consisting of elongation factor Tu, cochaperonin GroES-chaperonin GroEL, thioredoxin reductase, phosphoglycerate mutase, peroxiredoxin, glycerol-3-phosphate dehydrogenase, 2,3-butanediol dehydrogenase, fructose bisphosphate aldolase, and superoxide dismutase.

6. The method according to claim 1, wherein the bacterium has been further modified so that lactate dehydrogenase activity is decreased to 10% or less as compared to lactate dehydrogenase activity in an unmodified bacterium by disrupting or mutating a native lactate dehydrogenase gene.

7. The method according to claim 1, wherein the bacterium has been further modified so that a *Corynebacterium glutamicum* pyruvate carboxylase activity is enhanced; wherein enhanced activity is obtained by a method selected from the group consisting of:
  v) v)increasing the copy number of the pyruvate carboxylase gene,
  vi) modifying an expression control sequence of the pyruvate carboxylase gene,
  vii) replacing a promoter of the pyruvate carboxylase gene with a stronger promoter, and
  combinations thereof.

8. The method according to claim 1, wherein the organic acid is succinic acid.

9. The method according to claim 8, wherein the bacterium has been further modified so that a *Corynebacterium glutamicum* succinate dehydrogenase activity is enhanced; wherein enhanced activity is obtained by a method selected from the group consisting of
  viii) increasing the copy number of the succinate dehydrogenase gene,
  ix) modifying an expression control sequence of the succinate dehydrogenase gene,
  x) replacing a promoter of the succinate dehydrogenase gene with a stronger promoter, and
  combinations thereof.

10. The method according to claim 1, wherein the organic acid is malic acid or fumaric acid.

11. The method according to claim 10, wherein the bacterium has been further modified so that succinate dehydrogenase activity is decreased to 10% or less as compared to succinate dehydrogenase activity in an unmodified strain by disrupting or mutating a native succinate dehydrogenase gene.

12. A method for producing a succinic acid-containing polymer comprising:
  A) producing succinic acid by the method according to claim 1, and
  B) polymerizing the succinic acid.

* * * * *